US006188002B1

(12) United States Patent
Hall

(10) Patent No.: US 6,188,002 B1
(45) Date of Patent: Feb. 13, 2001

(54) INBRED CORN PLANT 01IZB2 AND SEEDS THEREOF

(75) Inventor: Michael A. Hall, Spencer, IA (US)

(73) Assignee: Dekalb Genetics Corporation, Dekalb, IL (US)

( * ) Notice: Under 35 U.S.C. 154(b), the term of this patent shall be extended for 0 days.

(21) Appl. No.: 09/265,349

(22) Filed: Mar. 9, 1999

Related U.S. Application Data

(62) Division of application No. 08/843,930, filed on Apr. 17, 1997, now Pat. No. 5,920,003, which is a continuation of application No. 08/784,182, filed on Jan. 15, 1997, now Pat. No. 5,856,614
(60) Provisional application No. 60/015,023, filed on Apr. 8, 1996.

(51) Int. Cl.$^7$ ............................ A01H 5/00; A01H 4/00; A01H 1/00; C12X 5/04
(52) U.S. Cl. ................. 800/320.1; 800/298; 800/275; 800/271; 800/268; 800/266; 800/301; 800/302; 800/303; 435/412; 435/424; 435/430; 435/430.1
(58) Field of Search .................. 800/320.1, 298, 800/275, 271, 301–303; 435/412, 424, 430, 430.1

(56) References Cited

U.S. PATENT DOCUMENTS

| | | |
|---|---|---|
| 3,903,645 | 9/1975 | Bradner . |
| 4,368,592 | 1/1983 | Welch ......................... 47/58 |
| 4,517,763 | 5/1985 | Beversdorf et al. ............. 47/58 |
| 4,581,847 | 4/1986 | Hibberd et al. ................ 47/58 |
| 4,594,810 | 6/1986 | Troyer ......................... 47/58 |
| 4,607,453 | 8/1986 | Troyer ......................... 47/58 |
| 4,626,610 | 12/1986 | Sun ............................ 800/1 |
| 4,627,192 | 12/1986 | Fick ........................... 47/58 |
| 4,629,819 | 12/1986 | Lindsey ....................... 800/1 |
| 4,642,411 | 2/1987 | Hibberd et al. ................ 800/1 |
| 4,654,465 | 3/1987 | Lindsey ....................... 800/1 |
| 4,658,084 | 4/1987 | Beversdorf et al. ............ 800/1 |
| 4,658,085 | 4/1987 | Beversdorf et al. ............ 800/1 |
| 4,677,246 | 6/1987 | Armond et al. ................ 800/1 |
| 4,686,319 | 8/1987 | Shifriss ...................... 800/1 |
| 4,731,499 | 3/1988 | Puskaric et al. ............... 800/1 |
| 4,737,596 | 4/1988 | Seifert et al. ................ 800/1 |
| 4,751,347 | 6/1988 | Erickson ...................... 800/1 |
| 4,767,888 | 8/1988 | Ayotte et al. ................. 800/1 |
| 5,276,263 | 1/1994 | Foley ........................ 800/200 |
| 5,856,614 | 1/1999 | Hall ......................... 800/200 |
| 5,920,003 | 7/1999 | Hall ........................ 800/320.1 |

FOREIGN PATENT DOCUMENTS 0 270 356   2/1987   (EP) .

OTHER PUBLICATIONS

Chandler et al., "Two Regulatory Genes of the Maize Anthocyanin Pathway Are Homologous: Isolation of B Utilizing R Genomic Sequences," *The Plant Cell*, 1:1175–1183, 1989.

Culotta, "How many Genes Had to Change to Produce Corn," *Science*, 252:1792–1793, 1991.
Duvick, "Genetic Contributions to Yield Gains of U.S. Hybrid Maize, 1930 to 1980," *Genetic Contributions to Yield Gains of Five Major Crop Plants*: Proceedings of a Symposium sponsored by Div. C–1, Crop Science Society of America, Dec. 2, 1981 in Atlanta, Georgia; W.R. Fehr, Crop Science Society of America and American Society of Agronomy, Madison, Wisconsin, pp. 15–47.
Green & Rhodes, "Plant Regeneration in Tissue Cultures of Maize," *Maize for Biological Research*, ed. W.F. Sheridan, A Special Publication of the Plant Molecular Biology Association, pp. 367–372, 1982.
Hauptmann et al., "Evaluation of Selectable Markers for Obtaining Stable Transformants in the Gramineae," *Plant Physiol.*, 86:602–606, 1988.
Larson & Hanway, "Corn Production," *Corn and Corn Improvement*, ed. G.F. Sprague, No. 18 in Agronomy Series, American Society of Agronomy, Inc., Madison, Wisconsin, pp. 625–669, 1977.
Ludwig et al., "A Regulatory Gene as a Novel Visible Marker for Maize Transformation," *Science*, 247:449–450, 1990.
Poehlman, *Breeding Field Crops*, 3rd ed., AVI Publishing Company, Westport, Connecticut, pp. 469–481, 1987.
Sprague & Eberhart, "Corn Breeding," *Corn and Corn Improvements*, ed. G.F. Sprague, No. 18 in Agronomy Series, American Society of Agronomy, Inc., Madison, Wisconsin, pp. 305–323, 1977.
Troyer, "A Retrospective View of Corn Genetic Resources," *Journal of Heredity*, 81:17–24, 1990.
Withers & King, "Proline: A Novel Cryoprotectant for the Freeze Preservation of Cultured Cells of *Zea mays* L.," *Plant Physiol.*, 64:675–578, 1979.
Armstrong & Green, "Establishment and Maintenance of Friable Embryogenic Maize Callus and the Involvement of L–Proline," *Planta*, 164:207–214, 1985.
Edallo et al., "Chromosomal Variation and Frequency of Spontaneous Mutation Associated with in vitro Culture and Plant Regeneration in Maize," *Maydica*, 26:39–56, 1981.

(List continued on next page.)

*Primary Examiner*—Gary Benzion
(74) *Attorney, Agent, or Firm*—Fulbright & Jaworski, L.L.P.

(57) ABSTRACT

According to the invention, there is provided inbred corn plants, separately designated 01DIB2 and O1IZB2. This invention thus relates to the plants, seeds and tissue cultures of the fore-mentioned inbred corn plants and to methods for producing a corn plant produced by crossing one of the inbred plants with itself or with another corn plant, such as another inbred. This invention further relates to corn seeds and plants produced by crossing any of the inbred plants 01DIB2 or 01IZB2 with another corn plant, such as another inbred, and to crosses with related species. This invention further relates to the inbred and hybrid genetic complements of the inbred corn plants 01DIB2 and 01IZB2, and also to the RFLP and genetic isozyme typing profiles of such inbred corn plants.

33 Claims, No Drawings

OTHER PUBLICATIONS

Gordon–Kamm et al., "Transformation of Maize Cells and Regeneration of Fertile Transgenic Plants," *The Plant Cell*, 2:603–618, 1990.

Green & Phillips, "Plant Regeneration from Tissue Cultures of Maize," *Crop Science*, 15:417–421, 1975.

Hallauer et al., "Corn Breeding," *Corn and Corn Improvement*, eds., Sprague et al., Madison, Wisconsin, Ch. 8, pp. 463–564, 1988.

MBS, Inc., *Genetics Handbook*, 17th ed., MBS, Inc., Ames, Iowa, pp. 3 & 19, 1990.

Meghji et al., "Inbreeding Depression, Inbred and Hybrid Grain Yields, and Other traits of Maize Genotypes Representing Three Eras," *Crop Science*, 24:545–549, 1984.

Phillips et al., "Cell/Tissue Culture and in vitro Manipulation," *Corn and Corn Improvement*, eds., Sprague et al., Ch. 5, pp. 345–387, 1988.

Rieger et al., *Glossary of Genetics and Cytogenetics, Classical and Molecular*, Springer–Verlag, Berlin, p. 116, 1976.

Rhodes et al., Genetically Transformed Maize Plants from Protoplasts, *Science*, 240:204–207, 1988.

Wright, "Commercial Hybrid Seed," *Hybridization of Crop Plants*, Fehr et al., eds. Am. Soc. of agron.–Crop Sci. Soc. of Am., Madison, Wisconsin, Ch. 8, pp. 161–176, 1980.

Wych, "Production of Hybrid Seed Corn," *Corn and Corn Improvement*, eds., Sprague et al., Madison, Wisconsin, Ch. 9, pp. 565–607, 1988.

Gerdes and Tracy, "Diversity of Historically Important Sweet Corn Inbredsas Estimated by RFLP's, Morphology, Isozymes, and Pedigree," *Crop Science*, 34(1):26–33, 1994.

Conger et al., "Somatic Embryogenesis from Cultured Leaf Segments of *Zea mays*," *Plant Cell Reports*, 6:345–347, 1987.

Duncan et al., "The Production of Callus Capable of Plant Regeneration from Immature Embryos of Numerous *Zea mays* Genotypes," *Planta*, 165:322–332, 1985.

Fehr (ed.), *Principles of Cultivar Development*, vol. 1: *Theory and Technique*, pp. 360–376, 1987.

Gaillard et al., "Optimization of Maize Microspore Isolation and Culture Condition for Reliable Plant Regeneration," *Plant Cell Reports*, 10(2):55, 1991.

Jensen, "Chromosome Doubling Techniques in Haploids," *Haploids and Higher Plants—Advances and Potentials, Proceedings of the First International Symposium*, University of Guelph, Jun. 10–14, 1974.

Nienhuis et al., "Restriction Fragment Length Polymorphism Analysis of Loci Associated with Insect Resistance in Tomato," *Crop Science*, 27:797–803, 1987.

Pace et al., "Anther Culture of Maize and the Visualization of Embryogenic Microspores by Fluorescent Microscopy," *Theoretical and Applied Genetics*, 73:863–869, 1987.

Poehlman & Sleper (eds), *Breeding Field Crops*, 4th Ed., pp. 172–175, 1995.

Rao et al., "Somatic Embryogenesis in Glume Callus Cultures," *Maize Genetics Cooperation Newsletter*, vol. 60, 1986.

Songstad et al. "Effect of 1–Aminocyclopropate–1–Carboxylic Acid, Silver Nitrate, and Norbornadiene on Plant Regeneration from Maize Callus Cultures," *Plant Cell Reports*, 7:262–265, 1988.

Stuber et al., "Techniques and scoring procedures for starch gel electrophoresis of enzymes of maize C. Zea mays, L.," *Tech. Bull.*, N. Carolina Agric. Res. Serv., vol. 286, 1988.

Wan et al., "Efficient Production of Doubled Haploid Plants Through Colchicine Treatment of Anther–Derived Maize Callus," *Theoretical and Applied Genetics*, 77:889–892, 1989.

Beckmann and Soller, "Restriction Fragment Length Polymorphisms in Plant Genetic Improvement," Oxford Surveys of Plant Molecular & Cell Biology, 3:196–250, 1986.

Smith and Smith, "Restriction Fragment Length Polymorphisms Can Differentiate Among U.S. Maize Hybrids," *Crop Sci.*, 31:893–899, 1991.

1994 Corn Seed Grower Option Contract for hybrid having 01DIB2 as an inbred parent.

1994 Corn Seed Grower Option Contract for hybrid having 01IZB2 as an inbred parent.

1996 Seed Corn Grower Contract (Experimental Production Contract).

1997 Seed Showcase for 2003929 (DK449), p. 6.

Declaration of R. Mark Lawson.

INBRED CORN PLANT 01IZB2 AND SEEDS THEREOF

This application is a divisional application of U.S. Ser. No. 08/843,930, filed Apr. 17, 1997 now issued as U.S. Pat. No. 5,920,003, which Application is a continuing application of U.S. Ser. No. 08/784,182 filed Jan. 15, 1997, now issued as U.S. Pat. No. 5,856,614, and of Provisional Application U.S. Ser. No. 60/015,023, filed Apr. 8, 1996.

BACKGROUND OF THE INVENTION

I. Technical Field of the Invention

The present invention relates to the field of corn breeding. In particular, the invention relates to inbred corn seed and plants designated 01DIB2 and 01IZB2, and derivatives and tissue cultures of such inbred plants.

II. Description of the Background Art

The goal of field crop breeding is to combine various desirable traits in a single variety/hybrid. Such desirable traits include greater yield, better stalks, better roots, resistance to insecticides, pests, and disease, tolerance to heat and drought, reduced time to crop maturity, better agronomic quality, and uniformity in germination times, stand establishment, growth rate, maturity, and fruit size.

Breeding techniques take advantage of a plant's method of pollination. There are two general methods of pollination: a plant self-pollinates if pollen from one flower is transferred to the same or another flower of the same plant. A plant cross-pollinates if pollen comes to it from a flower on a different plant.

Corn plants (*Zea mays* L.) can be bred by both self-pollination and cross-pollination. Both types of pollination involve the corn plant's flowers. Corn has separate male and female flowers on the same plant, located on the tassel and the ear, respectively. Natural pollination occurs in corn when wind blows pollen from the tassels to the silks that protrude from the tops of the ears.

Plants that have been self-pollinated and selected for type over many generations become homozygous at almost all gene loci and produce a uniform population of true breeding progeny, a homozygous plant. A cross between two such homozygous plants produce a uniform population of hybrid plants that are heterozygous for many gene loci. Conversely, a cross of two plants each heterozygous at a number of gene loci produces a population of hybrid plants that differ genetically and are not uniform. The resulting non-uniformity make performance unpredictable.

The development of uniform corn plant hybrids requires the development of homozygous inbred plants, the crossing of these inbred plants, and the evaluation of the crosses. Pedigree breeding and recurrent selection breeding methods are used to develop inbred plants from breeding populations. Those breeding methods combine the genetic backgrounds from two or more inbred plants or various other broad-based sources into breeding pools from which new inbred plants are developed by selfing and selection of desired phenotypes. The new inbreds are crossed with other inbred plants and the hybrids from these crosses are evaluated to determine which of those have commercial potential.

The pedigree breeding method for single-gene traits involves crossing two genotypes. Each genotype can have one or more desirable characteristics lacking in the other; or, each genotype can complement the other. If the two original parental genotypes do not provide all of the desired characteristics, other genotypes can be included in the breeding population. Superior plants that are the products of these crosses are selfed and selected in successive generations. Each succeeding generation becomes more homogeneous as a result of self-pollination and selection. Typically, this method of breeding involves five or more generations of selfing and selection: $S_1 \rightarrow S_2$; $S_2 \rightarrow S_3$; $S_3 \rightarrow S_4$; $S_4 \rightarrow S_5$, etc. After at least five generations, the inbred plant is considered genetically pure.

Backcrossing can also be used to improve an inbred plant. Backcrossing transfers a specific desirable trait from one inbred or other source to an inbred that lacks that trait. This can be accomplished for example by first crossing a superior inbred (A) (recurrent parent) to a donor inbred (non-recurrent parent), which carries the appropriate gene(s) for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other genes. The last backcross generation would be selfed to give pure breeding progeny for the gene(s) being transferred.

A single cross hybrid corn variety is the cross of two inbred plants, each of which has a genotype which complements the genotype of the other. The hybrid progeny of the first generation is designated $F_1$. Preferred $F_1$ hybrids are more vigorous than their inbred parents. This hybrid vigor, or heterosis, is manifested in many polygenic traits, including markedly improved higher yields, better stalks, better roots, better uniformity and better insect and disease resistance. In the development of hybrids only the $F_1$ hybrid plants are sought. An $F_1$ single cross hybrid is produced when two inbred plants are crossed. A double cross hybrid is produced from four inbred plants crossed in pairs (A×B and C×D) and then the two $F_1$ hybrids are crossed again (A×B)×(C×D).

The development of a hybrid corn variety involves three steps: (1) the selection of plants from various germ plasm pools; (2) the selfing of the selected plants for several generations to produce a series of inbred plants, which, although different from each other, each breed true and are highly uniform; and (3) crossing the selected inbred plants with unrelated inbred plants to produce the hybrid progeny ($F_1$). During the inbreeding process in corn, the vigor of the plants decreases. Vigor is restored when two unrelated inbred plants are crossed to produce the hybrid progeny ($F_1$). An important consequence of the homoygosity and homogeneity of the inbred plants is that the hybrid between any two inbreds is always the same. Once the inbreds that give a superior hybrid have been identified, hybrid seed can be reproduced indefinitely as long as the homogeneity of the inbred parents is maintained. Conversely, much of the hybrid vigor exhibited by $F_1$ hybrids is lost in the next generation ($F_2$). Consequently, seed from hybrid varieties is not used for planting stock. It is not generally beneficial for farmers to save seed of $F_1$ hybrids. Rather, farmers purchase $F_1$ hybrid seed for planting every year.

North American farmers plant over 70 million acres of corn at the present time and there are extensive national and international commercial corn breeding programs. A continuing goal of these corn breeding programs is to develop high-yielding corn hybrids that are based on stable inbred plants that maximize the amount of grain produced and minimize susceptibility to environmental stresses. To accomplish this goal, the corn breeder must select and develop superior inbred parental plants for producing hybrids.

SUMMARY OF THE INVENTION

In one aspect, the present invention provides corn plants designated, separately, 01DIB2 and 01IZB2. Also provided are corn plants having the physiological and morphological characteristics of corn plants 01DIB2 or 01IZB2, as exemplified by corn plants having all the physiological and morphological characteristics of corn plants 01DIB2 or 01IZB2.

The inbred corn plants of the invention may further comprise, or have, a cytoplasmic factor that is capable of conferring male sterility. Parts of the corn plants of the present invention are also provided, such as, e.g., pollen obtained from an inbred plant and an ovule of the inbred plant.

The invention also concerns seed of the corn plants 01DIB2 and 01IZB2, which have been deposited with the ATCC. The invention thus provides inbred corn seed designated 01IZB2 and having ATCC Accession No. 209836.

The inbred corn seed of the invention may be provided as essentially homogeneous populations of inbred corn seed designated 01IZB2. Essentially homogeneous populations of inbred seed are those that consist essentially of the particular inbred seed and are generally purified free from substantial numbers of other seed, so that the inbred seed forms between about 90% and about 100% of the total seed, and preferably, between about 95% and about 100% of the total seed. Most preferably, an essentially homogeneous population of inbred corn seed will contain between about 98.5%, 99%, 99.5% and about 100% of inbred seed, as measured by seed grow outs.

In any event, even if a population of inbred corn seed was found, for some reason, to contain about 50%, or even about 20% or 15% of inbred seed, this would still be distinguished from the small fraction of inbred seed that may be found within a population of hybrid seed, e.g., within a bag of hybrid seed. In such a bag of hybrid seed ordered for sale, the Governmental regulations require that the hybrid seed be at least about 95% of the total seed. In the practice of the present invention, the hybrid seed generally forms at least about 97% of the total seed. In the most preferred practice of the invention, the female inbred seed that may be found within a bag of hybrid seed will be about 1% of the total seed, or less, and the male inbred seed that may be found within a bag of hybrid seed will be negligible, i.e., will be on the order of about a maximum of 1 per 100,000, and usually less than this value.

The populations of inbred corn seed of the invention are further particularly defined as being essentially free from hybrid seed. The inbred seed populations may be separately grown to provide essentially homogeneous populations of inbred corn plants designated 01DIB2 or 01IZB2.

In another aspect, the present invention provides for single gene converted plants of 01DIB2 or 01IZB2. The single transferred gene may preferably be a dominant or recessive allele. Preferably, the single transferred gene will confer such traits as male sterility, herbicide resistance, insect resistance, resistance for bacterial, fungal, or viral disease, male fertility, enhanced nutritional quality, and industrial usage.

In another aspect, the present invention provides a tissue culture of regenerable cells of inbred corn plant 01DIB2 or 01IZB2. The tissue culture will preferably be capable of regenerating plants having the physiological and morphological characteristics of one of the foregoing inbred corn plants, and of regenerating plants having substantially the same genotype as one of the foregoing inbred corn plants. Preferably, the regenerable cells in such tissue cultures will be embryos, protoplasts, meristematic cells, pollen, leaves, anthers, roots, root tips, silk, flowers, kernels, ears, cobs, husks or stalks. Still further, the present invention provides corn plants regenerated from one of the tissue cultures of the invention.

In yet another aspect, the present invention provides processes for preparing corn seed or plants, which processes generally comprise crossing a first parent corn plant with a second parent corn plant, wherein at least one of the first or second parent corn plants is the inbred corn plant designated 01DIB2 or 01ZB2. These processes may be further exemplified as processes for preparing hybrid corn seed or plants, wherein a first inbred corn plant is crossed with a second, distinct inbred corn plant to provide a hybrid that has, as one of its parents, the inbred corn plant 01DIB2 or 01IZB2.

In a preferred embodiment, crossing comprises planting, in pollinating proximity, seeds of the first and second parent corn plant, and preferably, seeds of a first inbred corn plant and a second, distinct inbred corn plant; cultivating or growing the seeds of said first and second parent corn plants into plants that bear flowers; emasculating the male flowers of the first or second parent corn plant, i.e., treating the flowers so as to prevent pollen production, in order to produce an emasculated parent corn plant; allowing natural cross-pollination to occur between the first and second parent corn plants; and harvesting the seeds from the emasculated parent corn plant. Where desired, the harvested seed is grown to produce a corn plant or hybrid corn plant.

The present invention also provides corn seed and plants produced by a process that comprises crossing a first parent corn plant with a second parent corn plant, wherein at least one of the first or second parent corn plants is the inbred corn plant designated 01DIB2 or 01ZB2. In one embodiment, corn plants produced by the process are first generation ($F_1$) hybrid corn plants produced by crossing an inbred in accordance with the invention with another, distinct inbred. The present invention further contemplates seed of an $F_1$ hybrid corn plant.

In certain exemplary embodiments, the invention provides the following $F_1$ hybrid corn plants and seed thereof:

hybrid corn plant designated 2003929, having 01DIB2 and 01IZB2 as inbred parents.

In yet a further aspect, the invention provides inbred genetic complements of corn plants designated, separately, 01DIB2 and 01IZB2. The phrase "genetic complement" is used to refer to the aggregate of nucleotide sequences, the expression of which sequences defines the phenotype of, in the present case, a corn plant, or a cell or tissue of that plant. An inbred genetic complement thus represents the genetic make up of an inbred cell, tissue or plant, and a hybrid genetic complement represents the genetic make up of a hybrid cell, tissue or plant. The invention thus provides corn plant cells that have a genetic complement in accordance with the inbred corn plant cells disclosed herein, and plants, seeds and diploid plants containing such cells.

In another aspect, the present invention provides hybrid genetic complements, as represented by corn plant cells, tissues, plants and seeds, formed by the combination of a haploid genetic complement of an inbred corn plant of the invention with a haploid genetic complement of a second corn plant, preferably, another, distinct inbred corn plant. In another aspect, the present invention provides a corn plant regenerated from a tissue culture that comprises a hybrid genetic complement of this invention.

DETAILED DESCRIPTION OF THE PREFERRED EMBODIMENTS

I. Definitions

Barren Plants: Plants that are barren, i.e., lack an ear with grain, or have an ear with only a few scattered kernels.

Cg: *Colletotrichum graminicola* rating. Rating times 10 is approximately equal to percent total plant infection.

CLN: Corn lethal necrosis (combination of Maize Chlorotic Mottle Virus and Maize Dwarf Mosaic virus) rating: numerical ratings are based on a severity scale where 1=most resistant to 9=susceptible.

Cn: *Corynebacterium nebraskense* rating. Rating times 10 is approximately equal to percent total plant infection.

Cz: *Cercospora zeae-maydis* rating. Rating times 10 is approximately equal to percent total plant infection.

Dgg: *Diatraea grandiosella* girdling rating (values are percent plants girdled and stalk lodged).

Dropped Ears: Ears that have fallen from the plant to the ground.

Dsp: Diabrotica species root ratings (1=least affected to 9=severe pruning).

Ear-Attitude: The attitude or position of the ear at the vest scored as upright, horizontal, or pendant.

Ear-Diameter: The average diameter of the ear at its midpoint.

Ear-Dry Husk Color: The color of the husks at harvest scored as buff, red, or purple.

Ear-Cob Color: The color of the cob, scored as white, pink, red, or brown.

Ear-Cob Diameter: The average diameter of the cob measured at the midpoint.

Ear-Cob Strength: A measure of mechanical strength of the cobs to breakage, scored as strong or weak.

Ear-Fresh Husk Color: The color of the husks 1 to 2 weeks after pollination scored as green, red, or purple.

Ear-Husk Bract: The length of an average husk leaf scored as short, medium, or long.

Ear-Husk Cover: The average distance from the tip of the ear to the tip of the husks. Minimum value no less than zero.

Ear-Husk Opening: An evaluation of husk tightness at harvest scored as tight, intermediate, or open.

Ear-Length: The average length of the ear.

Ear-Number Per Stalk: The average number of ears per plant.

Ear-Shank Internodes: The average number of internodes on the ear shank.

Ear-Shank Length: The average length of the ear shank.

Ear-Shelling Percent: The average of the shelled grain weight divided by the slum of the shelled grain weight and cob weight for a single ear.

Ear-Silk Color: The color of the silk observed 2 to 3 days after silk emergence scored as green-yellow, yellow, pink, red, or purple.

Ear-Taper (Shape): The taper or shape of the ear scored as conical, semi-conical, or cylindrical.

Ear-Weight: The average weight of an ear.

Early Stand: The percent of plants that emerge from the ground as determined in the early spring.

ER: Ear rot rating (values approximate percent ear rotted).

Final Stand Count: The number of plants just prior to harvest.

GDUs to Shed: The number of growing degree units (GDUs) or heat units required for an inbred line or hybrid to have approximately 50 percent of the plants shedding pollen as measured from time of planting. Growing degree units are calculated by the Barger Method, where the heat units for a 24-hour period are calculated as GDUs=[Maximum daily temperature+Minimum daily temperature)/2]−50. The highest maximum daily temperature used is 86 degrees Fahrenheit and the lowest minimum temperature used is 50 degrees Fahrenheit. GDUs to shed is then determined by summuing the individual daily values from planting date to the date of 50 percent pollen shed.

GDUs to Silk: The number of growing degree units for an inbred line or hybrid to have approximately 50 percent of the plants with silk emergence as measured from time of planting. Growing degree units are calculated by the same methodology as indicated in the GDUs to shed definition.

Hc2: *Helminthosporium carbonum* race 2 rating. Rating times 10 is approximately equal to percent total plant infection.

Hc3: *Helminthosporium carbonum* race 3 rating. Rating times 10 is approximately equal to percent total plant infection.

Hm: *Helminthosporium maydis* race 0 rating. Rating times 10 is approximately equal to percent total plant infection.

Ht1: *Helminthosporium turcicum* race 1 rating. Rating times 10 is approximately equal to percent total plant infection.

Ht2: *Helminthosporium turcicum* race 2 rating. Rating times 10 is approximately equal to percent total plant infection.

HtG: +=Presence of Ht chlorotic-lesion type resistance. Rating times 10 is approximately equal to percent total plant infection.

−=Absence of a Ht chlorotic-lesion type resistance. Rating times 10 is approximately equal to percent total plant infection.

±=Segregation of a Ht chlorotic-lesion type resistance. Rating times 10 is approximately equal to percent total plant infection.

Kernel-Aleurone Color: The color of the aleurone scored as white, pink, tan, brown, bronze, red, purple, pale purple, colorless, or variegated.

Kernel-Cap Color: The color of the kernel cap observed at dry stage, scored as white, lemon-yellow, yellow or orange.

Kernel-Endosperm Color: The color of the endosperm scored as white, pale yellow, or yellow.

Kernel-Endosperm Type: The type of endosperm scored as normal, waxy, or opaque.

Kernel-Grade: The percent of kernels that are classified as rounds.

Kernel-Length: The average distance from the cap of the kernel to the pedicel.

Kernel-Number Per Row: The average number of kernels in a single row.

Kernel-Pericarp Color: The color of the pericarp scored as colorless, red-white crown, tan, bronze, brown, light red, cherry red, or variegated.

Kernel-Row Direction: The direction of the kernel rows on the ear scored as straight, slightly curved, spiral, or indistinct (scattered).

Kernel-Row Number: The average number of rows of kernels on a single ear.

Kernel-Side Color: The color of the kernel side observed at the dry stage, scored as white, pale yellow, yellow, orange, red, or brown.

Kernel-Thickness: The distance across the narrow side of the kernel.

Kernel-Type: The type of kernel scored as dent, flint, or intermediate.

Kernel-Weight: The average weight of a predetermined number of kernels.

Kernel-Width: The distance across the flat side of the kernel.

Kz: *Kabatiella zeae* rating. Rating times 10 is approximately equal to percent toted plant Infection.

Leaf-Angle: Angle of the upper leaves to the stalk scored as upright (0 to 30 degrees), intermediate (30 to 60 degrees), or lax (60 to 90 degrees).

Leaf-Color: The color of the leaves 1 to 2 weeks after pollination scored as light green, medium green, dark green, or very dark green.

Leaf-Length: The average length of the primary ear leaf.

Leaf-Longitudinal Creases: A rating of the number of longitudinal creases on the leaf surface 1 to 2 weeks after pollination. Creases are scored as absent, few, or many.

Leaf-Marginal Waves: A rating of the waviness of the leaf margin 1 to 2 weeks after pollination. Rated as none, few, or many.

Leaf-Number: The average number of leaves of a mature plant. Counting begins with the cotyledonary leaf and ends with the flag leaf.

Leaf-Sheath Anthocyanin: A rating of the level of anthocyanin in the leaf sheath 1 to 2 weeks after pollination, scored as absent, basal-weak, basal-strong, weak or strong.

Leaf-Sheath Pubescence: A rating of the pubescence of the leaf sheath. Ratings are taken 1 to 2 weeks after pollination and scored as light, medium, or heavy.

Leaf-Width: The average width of the primary ear leaf measured at its widest point.

LSS: Late season standability (values times 10 approximate percent plants lodged in disease evaluation plots).

Moisture: The moisture of the grain at harvest.

On1: *Ostrinia nubilalis* 1st brood rating (1=resistant to 9=susceptible).

On2: *Ostrinia nubilalis* 2nd brood rating (1=resistant to 9=susceptible).

Relative Maturity: A maturity rating based on regression analysis. The regression analysis is developed by utilizing check hybrids and their previously established day rating versus actual harvest moistures. Harvest moisture on the hybrid in question is determined and that moisture value is inserted into the regression equation to yield a relative maturity.

Root Lodging: Root lodging is the percentage of plants that root lodge. A plant is counted as root lodged if a portion of the plant leans from the vertical axis by approximately 30 degrees or more.

Seedling Color: Color of leaves at the 6 to 8 leaf stage.

Seedling Height: Plant height at the 6 to 8 leaf stage.

Seedling Vigor: A visual rating of the amount of vegetative growth on a 1 to 9 scale, where 9 equals best. The score is taken when the average entry in a trial is at the fifth leaf stage.

Selection Index: The selection index gives a single measure of hybrid's worth based on information from multiple traits. One of the traits that is almost always included is yield. Traits may be weighted according to the level of importance assigned to them.

Sr: *Sphacelotheca reiliana* rating is actual percent infection.

Stalk-Anthocyanin: A rating of the amount of anthocyanin pigmentation in the stalk. The stalk is rated 1 to 2 weeks after pollination as absent, basal-weak, basal-strong, weak, or strong.

Stalk-Brace Root Color: The color of the brace roots observed 1 to 2 weeks after pollination as green, red, or purple.

Stalk-Diameter: The average diameter of the lowest visible internode of the stalk.

Stalk-Ear Height: The average height of the ear measured from the ground to the point of attachment of the ear shank of the top developed ear to the stalk.

Stalk-Internode Direction: The direction of the stalk internode observed after pollination as straight or zigzag.

Stalk-Internode Length: The average length of the internode above the primary ear.

Stalk Lodging: The percentage of plants that did stalk lodge. Plants are counted as stalk lodged if the plant is broken over or off below the ear.

Stalk-Nodes With Brace Roots: The average number of nodes having brace roots per plant.

Stalk-Plant Height: The average height of the plant as measured from the soil to the tip of the tassel.

Stalk-Tillers: The percent of plants that have tillers. A tiller is defined as a secondary shoot that has developed as a tassel capable of shedding pollen.

Staygreen: Staygreen is a measure of general plant health near the time of black layer formation (physiological maturity). It is usually recorded at the time the ear husks of most entries within a trial have turned a mature color. Scoring is on a 1 to 9 basis where 9 equals best.

STR: Stalk rot rating (values represent severity rating of 1=25 percent of inoculated internode rotted to 9=entire stalk rotted and collapsed).

SVC: Southeastern Virus Complex combination of Maize Chlorotic Dwarf Virus and Maize Dwarf Mosaic Virus) rating; numerical ratings are based on a severity scale where 1=most resistant to 9=susceptible (1988 reactions are largely Maize Dwarf Mosaic Virus reactions).

Tassel-Anther Color: The color of the anthers at 50 percent pollen shed scored as green-yellow, yellow, pink, red, or purple.

Tassel-Attitude: The attitude of the tassel after pollination scored as open or compact.

Tassel-Branch Angle: The angle of an average tassel branch to the main stem of the tassel scored as upright (less than 30 degrees), intermediate (30 to 45 degrees), or lax (greater than 45 degrees).

Tassel-Branch Number: The average number of primary tassel branches.

Tassel-Glume Band: The closed anthocyanin band at the base of the glume scored as present or absent.

Tassel-Glume Color: The color of the glumes at 50 percent shed scored as green, red, or purple.

Tassel-Length: The length of the tassel measured from the base of the bottom tassel branch to the tassel tip.

Tassel-Peduncle Length: The average length of the tassel peduncle, measured from the base of the flag leaf to the base of the bottom tassel branch.

Tassel-Pollen Shed: A visual rating of pollen shed determined by tapping the tassel and observing the pollen flow of approximately five plants per entry. Rated on a 1 to 9 scale where 9=sterile, 1=most pollen.

Tassel-Spike Length: The length of the spike measured from the base of the top tassel branch to the tassel tip.

Test Weight: The measure of Eve weight of the grain in pounds for a given volume (bushel) adjusted to 15.5 percent moisture.

Yield: Yield of grain at harvest adjusted to 15.5 percent moisture.

II. Other Definitions

Allele is any of one or more alternative forms of a gene, all of which alleles relate to one trait or characteristic. In a diploid cell or organism, the two alleles of a given gene occupy corresponding loci on a pair of homologous chromosomes.

Backcrossing is a process in which a breeder crosses a first generation hybrid ($F_1$) with one of the parental genotypes.

Chromatography is a technique wherein a mixture of dissolved substances are bound to a solid support followed by passing a column of fluid across the solid support and varying the composition of the fluid. The components of the mixture are separated by selective elution.

Crossing refers to the mating of two parent plants.

Cross-pollination refers to fertilization by the union of two gametes from different plants.

Diploid refers to a cell or organism having two sets of chromosomes.

Electrophoresis is a process by which particles suspended in a fluid are moved under the action of an electrical field, and thereby separated according to their charge and molecular weight. This method of separation is well known to those skilled in the art and is typically applied to separating various forms of enzymes and of DNA fragments produced by restriction endonucleases.

Emasculate refers to the removal of plant male sex organs.

Enzymes are organic catalysts that can exist in various forms called isozymes.

$F_1$ Hybrid refers to the first generation progeny of the cross of two plants.

Genetic Complement refers to an aggregate of nucleotide sequences, the expression of which sequences defines the phenotype in corn plants, or components of plants including cells or tissue.

Genotype refers to the genetic constitution of a cell or organism.

Haploid refers to a cell or organism having one set of the two sets of chromosomes in a diploid.

Isozymes are one of a number of enzymes which catalyze the same reaction(s) but differ from each other, e.g., in primary structure and/or electrophoretic mobility. The differences between isozymes are under single gene, codominant control. Consequently, electrophoretic separation to produce band patterns can be equated to different alleles at the DNA level. Structural differences that do not alter charge cannot be detected by this method.

Isozyme typing profile refers to a profile of band patterns of isozymes separated by electrophoresis that can be equated to different alleles at the DNA level.

Linkage refers to a phenomenon wherein alleles on the same chromosome tend to segregate together more often than expected by chance if their transmission was independent.

Marker is a readily detectable phenotype, preferably inherited in codominant fashion (both alleles at a locus in a diploid heterozygote are readily detectable), with no environmental variance component, i.e., heritability of 1.

01IZB2 refers to the corn plant from which seeds having ATCC Accession No. 209836 were obtained, as well as plants grown from those seeds.

Phenotype refers to the detectable characteristics of a cell or organism, which characteristics are the manifestation of gene expression.

Quantitative Trait Loci (QTL) refer to genetic loci that control to some degree numerically representable traits that are usually continuously distributed.

Regeneration refers to the development of a plant from tissue culture.

RFLP genetic marker profile refers to a profile of band patterns of DNA fragment lengths typically separated by agarose gel electrophoresis, after restriction endonuclease digestion of DNA.

Self-pollination refers to the transfer of pollen from the anther to the stigma of the same plant.

Single Gene Converted (Conversion) Plant refers to plants which are developed by a plant breeding technique called backcrossing wherein essentially all of the desired morphological and physiological characteristics of an inbred are recovered in addition to the single gene transferred into the inbred via the backcrossing technique.

Tissue Culture refers to a composition comprising isolated cells of the same or a different type or a collection of such cells organized into parts of a plant.

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

III. Inbred Corn Plant 01DIB2

In accordance with one aspect of the present invention, there is provided a novel inbred corn plant, designated 01DIB2. Inbred corn plant 01DIB2 is a yellow, dent corn inbred that can be compared to inbred corn plants 2FACC and 91BMA2, both proprietary inbreds of DeKalb Genetics Corporation. 01DIB2 differs significantly (at the 1% level) from these inbred lines in several aspects (See Tables 1 and 2).

TABLE 1

COMPARISON OF 01DIB2 WITH 2FACC

| INBRED | BARREN % | DROP % | EHT INCH | FINAL | MST % | PHT INCH | RTL % | SHED GDU | SILK GDU | STL % | YLD BU/A |
|---|---|---|---|---|---|---|---|---|---|---|---|
| 01DIB2 | 0.2 | 0.1 | 28.5 | 53.3 | 18.5 | 61.5 | 1.9 | 1362.6 | 1412.7 | 2.8 | 84.1 |
| 2FACC | 0.2 | 0.0 | 31.4 | 58.6 | 21.0 | 68.7 | 1.8 | 1463.2 | 1465.1 | 1.8 | 82.2 |
| DIFF | 0.0 | 0.1 | −2.9 | −5.4 | −2.5 | −7.2 | 0.0 | −100.6 | −118.3 | 1.1 | 1.9 |
| # LOC | 0.2 | 12 | 12 | 12 | 11 | 12 | 12 | 12 | 12 | 12 | 12 |
| P VALUE | 0.81 | 0.92 | 0.01** | 0.04* | 0.00** | 0.00** | 0.85 | 0.00** | 0.00** | 0.60 | 0.66 |

Significance levels are indicated as: + = 10 percent, * = 5 percent, ** = 1 percent.

Legend Abbreviations:
BARREN % = Barren Plants (percent)
DROP % = Dropped Ears (percent)
EHT INCH = Ear Height (inches)
FINAL = Final Stand
MST % = Moisture (percent)
PHT INCH = Plant Height (inches)
RTL % = Root Lodging (percent)
SHED GDU = GDUs to Shed
SILK GDU = GDUS to Silk
STL % = Stalk Lodging (percent)
YLD BU = Yield (bushels/acre)

TABLE 2

COMPARISON OF 01DIB2 WITH 91BMA2

| INBRED | BARREN % | DROP % | EHT INCH | FINAL | MST % | PHT INCH | RTL % | SHED GDU | SILK GDU | STL % | YLD BU/A |
|---|---|---|---|---|---|---|---|---|---|---|---|
| 01DIB2 | 0.1 | 0.1 | 26.8 | 48.5 | 17.7 | 58.3 | 2.2 | 1391.2 | 1376.7 | 3.5 | 65.5 |
| 91BMA2 | 0.7 | 0.0 | 28.0 | 53.3 | 17.4 | 65.8 | 0.3 | 1403.8 | 1401.5 | 1.2 | 59.1 |
| DIFF | −0.6 | 0.1 | −1.2 | −4.7 | 0.3 | −7.4 | 1.9 | −12.7 | −24.8 | 2.3 | 6.4 |
| # LOC | 6 | 6 | 6 | 6 | 5 | 6 | 6 | 6 | 6 | 6 | 6 |
| P VALUE | 0.20 | 0.90 | 0.47 | 0.30 | 0.77 | 0.00** | 0.34 | 0.56 | 0.28 | 0.42 | 0.39 |

Significance levels are indicated as: + = 10 percent, * = 5 percent, ** = 1 percent.
Legend Abbreviations:
BARREN % = Barren Plants (percent)
DROP % = Dropped Ears (percent)
EHT INCH = Ear Height (inches)
FINAL = Final Stand
MST % = Moisture (percent)
PHT INCH = Plant Height (inches)
RTL % = Root Lodging (percent)
SHED GDU = GDUs to Shed
SILK GDU = GDUS to Silk
STL % = Stalk Lodging (percent)
YLD BU = Yield (bushels/acre)

A. Origin and Breeding History

Inbred plant 01DIB2 was derived from the cross of two inbred plants designated 2FACC and BMF1.

01DIB2 shows uniformity and stability within the limits of environmental influence for the traits described hereinafter in Table 3. 01DIB2 has been self-pollinated and ear-rowed a sufficient number of generations with careful attention paid to uniformity of plant type to ensure homozygosity and phenotypic stability. No variants have been observed or are expected in 01DIB2.

Inbred corn plants can be reproduced by planting such inbred seeds, growing the resulting corn plants under self-pollinating or sib-pollinating conditions with adequate isolation using standard techniques well known to an artisan skilled in the agricultural arts. Seeds can be harvested from such a plant using standard, well known procedures.

The origin and breeding history of inbred plant 01DIB2 can be summarized as follows:

| | |
|---|---|
| Winter 1988–9 | The backcross 2FACC**BMF1 was made (nursery rows 8W:100-77, 78). |
| Summer 1989 | The S1 generation was grown and selfed (nursery rows 89:1-86 through 2-91). |
| Summer 1990 | The S2 generation was grown and selfed (nursery row 90:17-47). |
| Summer 1991 | The S3 generation was grown and selfed (nursery row 91:95-45). |
| Summer 1992 | The S4 generation was grown and selfed (nursery row 92:108-30). The inbred was coded as 01DIB2. |
| Winter 1992–3 | The S5 generation was grown and selfed (nursery row 2W:N21-27). |
| Summer 1993 | The S6 generation was grown and selfed (nursery rows 93:216-46). |
| Winter 1993–4 | The S7 generation was grown and selfed. Two ear-to-row selections were bulked (nursery rows 3W:ADM-440, 443) as the final selection of 01DIB2. |

B. Phenotypic Description

In accordance with another aspect of the present invention, there is provided a corn plant having the physiological and morphological characteristics of corn plant 01DIB2. A description of the physiological and morphological characteristics of corn plant 01DIB2 is presented in Table 3. These traits can be compared to inbred corn plants 2FACC and 91BMA2.

TABLE 3

MORPHOLOGICAL TRAITS FOR THE 01DIB2 PHENOTYPE

| CHARACTERISTIC | 01DIB2 | 2FACC | 91BMA2 |
|---|---|---|---|
| 1. STALK | | | |
| Diameter (width) cm. | 2.1 | 2.2 | 1.8 |
| Anthocyanin | basal-strong | weak | absent |
| Nodes With Brace Roots | 1.3 | 1.8 | 1.1 |
| Brace Root Color | red | purple | — |
| Internode Direction | straight | — | straight |
| Internode Length cm. | 10.9 | 12.8 | 12.1 |
| 2. LEAF | | | |
| Number | 18.8 | 20.1 | 19.0 |
| Color | med. green | med. green | med. green |
| Length cm. | 71.5 | 72.8 | 65.5 |
| Width cm. | 9.0 | 8.9 | 8.4 |
| Sheath Anthocyanin | weak | weak | — |
| Marginal Waves | medium | few | few |
| Longitudinal Creases | few | few | few |
| 3. TASSEL | | | |
| Attitude | compact | compact | — |
| Length cm. | 22.9 | 26.3 | 32.0 |
| Spike Length cm. | 16.6 | 18.5 | 23.2 |
| Peduncle Length cm. | 4.9 | 5.1 | 7.7 |
| Branch Number | 6.6 | 7.2 | 4.0 |
| Anther Color | green/yellow | pink | — |
| Glume Color | green | green | green |
| Glume Band | absent | absent | absent |
| 4. EAR | | | |
| Number Per Stalk | 1.3 | 1.1 | 1.1 |
| Position (attitude) | upright | upright | upright |
| Length cm. | 15.2 | 13.7 | 13.5 |
| Shape | semi-conical | semi-conical | semi-conical |
| Diameter cm. | 3.8 | 4.3 | 3.4 |
| Weight gm. | 111.6 | 117.8 | 92.5 |
| Shank Length cm. | 12.5 | 15.4 | 13.9 |
| Shank Internode Number | 5.3 | 6.6 | 6.4 |
| Husk Bract | short | short | short |
| Husk Cover cm. | 3.9 | 6.8 | 5.9 |
| Husk Color Fresh | green | green | green |
| Husk Color Dry | buff | buff | buff |
| Cob Diameter cm. | 2.0 | 2.5 | 2.0 |
| Shelling Percent | 85.2 | 81.8 | 82.7 |

TABLE 3-continued

MORPHOLOGICAL TRAITS FOR THE 01DIB2 PHENOTYPE

| CHARACTERISTIC | 01DIB2 | 2FACC | 91BMA2 |
|---|---|---|---|
| 5. KERNEL | | | |
| Row Number | 13.3 | 15.1 | 12.7 |
| Number Per Row | 31.7 | 25.9 | 27.8 |
| Row Direction | curved | curved | curved |
| Type | dent | dent | intermediate |
| Cap Color | yellow | yellow | yellow |
| Side Color | orange | deep yellow | orange |
| Length (depth) mm. | 11.1 | 10.7 | 9.6 |
| Width mm. | 8.5 | 8.0 | 7.4 |
| Thickness | 4.4 | 4.1 | 3.5 |
| Weight of 1000K gm. | 263.5 | 279.1 | 225.3 |
| Endosperm Type | normal | normal | normal |
| Endosperm Color | yellow | yellow | yellow |

*These are typical values. Values may vary due to environment. Other values that are substantially equivalent are also within the scope of the invention. Substantially equivalent refers to quantitative traits that when compared do not show statistical differences of their means.

IV. Inbred Corn Plant 01IZB2

In accordance with one aspect of the present invention, there is provided a novel inbred corn plant, designated 01IZB2. Inbred corn plant 01IZB2 is a yellow, dent corn inbred that can be compared to inbred corn plants 01IBH2, and 3IIH6, both proprietary inbreds of DeKalb Genetics Corporation. 01IZB2 differs significantly (at the 1% level) from these inbred lines in several aspects (See Tables 4 and 5)

TABLE 4

COMPARISON OF 01IZB2 WITH 01IBH2

| INBRED | BARREN % | DROP % | EHT INCH | FINAL | MST % | PHT INCH | RTL % | SHED GDU | SILK GDU | STL % | YLD BU/A |
|---|---|---|---|---|---|---|---|---|---|---|---|
| 01IZB2 | 0.5 | 0.4 | 29.8 | 52.3 | 13.7 | 61.3 | 0.4 | 1420.0 | 1508.8 | 0.9 | 67.0 |
| 01IBH2 | 0.5 | 0.0 | 31.6 | 55.9 | 20.7 | 64.1 | 0.6 | 1487.0 | 1499.3 | 1.9 | 67.7 |
| DIFF | 0.0 | 0.4 | −1.8 | −3.6 | −7.0 | −2.8 | −0.2 | −67.0 | 9.5 | −1.1 | −0.7 |
| # LOC | 6 | 6 | 6 | 6 | 2 | 6 | 6 | 6 | 6 | 6 | 5 |
| P VALUE | 1.00 | 0.62 | 0.26 | 0.43 | 0.00** | 0.19 | 0.93 | 0.00** | 0.68 | 0.70 | 0.93 |

Significance levels are indicated as: + = 10 percent, * = 5 percent, ** = 1 percent.
Legend Abbreviations:
BARREN % = Barren Plants (percent)
DROP % = Dropped Ears (percent)
EHT INCH = Ear Height (inches)
FINAL = Final Stand
MST % = Moisture (percent)
PHT INCH = Plant Height (inches)
RTL % = Root Lodging (percent)
SHED GDU = GDUs to Shed
SILK GDU = GDUS to Silk
STL % = Stalk Lodging (percent)
YLD BU = Yield (bushels/acre)

TABLE 5

COMPARISON OF 01IZB2 WITH 3IIH6

| INBRED | BARREN % | DROP % | EHT INCH | FINAL | MST % | PHT INCH | RTL % | SHED GDU | SILK GDU | STL % | YLD BU/A |
|---|---|---|---|---|---|---|---|---|---|---|---|
| 01IZB2 | 0.8 | 0.2 | 30.0 | 54.0 | 15.0 | 63.3 | 0.3 | 1392.6 | 1477.9 | 1.8 | 63.6 |

TABLE 5-continued

COMPARISON OF 01IZB2 WITH 3IIH6

| 3IIH6 | 0.3 | 0.2 | 29.1 | 53.2 | 17.8 | 65.4 | 0.5 | 1433.6 | 1459.3 | 2.5 | 70.5 |
|---|---|---|---|---|---|---|---|---|---|---|---|
| DIFF | 0.4 | 0.0 | 0.9 | 0.8 | −2.8 | −2.0 | −0.2 | −41.0 | 18.6 | −0.7 | −6.9 |
| # LOC | 27 | 27 | 27 | 27 | 11 | 27 | 27 | 27 | 27 | 27 | 27 |
| P VALUE | 0.42 | 0.94 | 0.27 | 0.81 | 0.00** | 0.04* | 0.79 | 0.00** | 0.05* | 0.67 | 0.03* |

Significance levels are indicated as: + = 10 percent, * = 5 percent, ** = 1 percent.
Legend Abbreviations:
BARREN % = Barren Plants (percent)
DROP % = Dropped Ears (percent)
EHT INCH = Ear Height (inches)
FINAL = Final Stand
MST % = Moisture (percent)
PHT INCH = Plant Height (inches)
RTL % = Root Lodging (percent)
SHED GDU = GDUs to Shed
SILK GDU = GDUS to Silk
STL % = Stalk Lodging (percent)
YLD BU = Yield (bushels/acre)

A. Origin and Breeding History

Inbred plant 01IZB2 was derived from the cross between a line derived from Pioneer 3615 and the Pioneer hybrid 3790.

01IZB2 shows uniformity and stability within the limits of environmental influence for the traits described hereinafter in Table 6. 01IZB2 has been self-pollinated and ear-rowed a sufficient number of generations with careful attention paid to uniformity of plant type to ensure homozygosity and phenotypic stability. No variant traits have been observed or are expected in 01IZB2.

A deposit of 2500 seeds of plant designated 01IZB2 has been made with the American Type Culture Collection (ATCC), 10801 University Blvd., Manassas, Va., 20110-2209, on May 4, 1998. Those deposited seeds have been assigned Accession No. 209836. The deposit was made in accordance with the terms and provisions of the Budapest Treaty relating to deposit of microorganisms and is made for a term of at least thirty (30) years and at least five (05) years after the most recent request for the furnishing of a sample of the deposit was received by the depository.

Inbred corn plants can be reproduced by planting such inbred seeds, growing the resulting corn plants under self-pollinating or sib-pollinating conditions with adequate isolation using standard techniques well known to an artisan skilled in the agricultural arts. Seeds can be harvested from such a plant using standard, well known procedures.

The origin and breeding history of inbred plant 01IZB2 can be summarized as follows:

| | |
|---|---|
| Summer 1987 | The cross was made between a line derived from the Pioneer hybrid 3615 and the Pioneer hybrid 3790. |
| Summer 1988 | The S1 generation was grown and selfed (nursery rows 88:10-37 through 10-18). |
| Winter 1988–9 | The S2 generation was grown and selfed (nursery row 8W:541-12). |
| Summer 1989 | The S3 generation was grown and selfed (nursery row 89:87-54). |
| Winter 1990–1 | The S4 generation was grown and selfed (nursery row 0W:P54-29). |
| Summer 1991 | The S5 generation was grown and selfed (nursery row 91:206-84). The inbred coded was 01IZB2. Red and white cob segregation was occurring. |
| Summer 1992 | The S6 generation was grown and selfed. One red cobbed ear-to-row selection was kept (nursery row 92:139-21). |
| Summer 1993 | The S7 generation was grown and selfed. 30 ear-to-row red cobbed selections were kept (nursery rows 93:218-84 through 93:218-65). |
| Winter 1993–4 | The S8 generation was grown and selfed. 20 red cobbed ear-to-row selections were made (nursery rows 3W:ADM-404, 406, 415, 416, 417, 418, 419, 421, and 422). |
| Summer 1994 | The S9 generation was grown and selfed. Final selection of red cobbed ears was made by bulking (nursery rows 94:314-9, 8, 7, 6, 5, 2, 315-3, 4, 6, 7, 8, 9). |

B. Phenotypic Description

In accordance with another aspect of the present invention, there is provided a corn plant having the physiological and morphological characteristics of corn plant 01IZB2. A description of the physiological and morphological characteristics of corn plant 01IZB2 is presented in Table 6. These traits can be compared to inbred corn plants 01IBH2 and 3IIH6.

TABLE 6

MORPHOLOGICAL TRAITS FOR THE 01IZB2 PHENOTYPE

| CHARACTERISTIC | 01IZB2 | 01IBH2 | 3IIH6 |
|---|---|---|---|
| 1. STALK | | | |
| Diameter (width) cm. | 2.7 | 2.1 | 2.3 |
| Nodes With Brace Roots | 1.8 | 1.1 | 0.7 |
| Brace Root Color | green | green | — |
| Internode Length cm. | 15.7 | 14.4 | 13.1 |
| 2. LEAF | | | |
| Number | 17.5 | 17.3 | 18.8 |
| Color | med. green | med. green | med. green |
| Length cm. | 80.1 | 68.2 | 70.5 |
| Width cm. | 8.0 | 8.9 | 8.0 |
| Sheath Pubescence | light | heavy | — |
| Marginal Waves | few | few | few |
| Longitudinal Creases | few | absent | — |
| 3. TASSEL | | | |
| Length cm. | 37.6 | 33.6 | 35.3 |
| Spike Length cm. | 22.4 | 23.1 | 25.2 |
| Peduncle Length cm. | 9.3 | 8.2 | 7.6 |
| Branch Number | 12.3 | 7.8 | 12.9 |
| Anther Color | red | green-yellow | — |
| Glume Color | green | green | — |
| Glume Band | absent | absent | absent |
| 4. EAR | | | |
| Silk Color | pink | — | red |
| Number Per Stalk | 1.3 | 1.0 | 1.4 |

TABLE 6-continued

MORPHOLOGICAL TRAITS FOR THE 01IZB2 PHENOTYPE

| CHARACTERISTIC | 01IZB2 | 01IBH2 | 3IIH6 |
|---|---|---|---|
| Length cm. | 16.1 | 14.6 | 15.6 |
| Shape | semi-conical | semi-conical | semi-conical |
| Diameter cm. | 3.9 | 4.0 | 3.9 |
| Weight gm. | 117.7 | 103.2 | 107.6 |
| Shank Length cm. | 16.1 | 10.1 | 9.6 |
| Shank Internode Number | 6.2 | 6.9 | 5.6 |
| Husk Cover cm. | 5.3 | 4.4 | 3.7 |
| Husk Color Fresh | green | green | green |
| Husk Color Dry | buff | buff | buff |
| Cob Diameter cm. | 2.0 | 2.3 | 2.1 |
| Shelling Percent | 83.4 | 89.0 | 83.3 |
| 5. KERNEL | | | |
| Row Number | 14.4 | 16.3 | 15.3 |
| Number Per Row | 29.6 | 29.3 | 29.7 |
| Type | dent | dent | — |
| Cap Color | yellow | yellow | yellow |
| Side Color | orange | orange | — |
| Length (depth) mm. | 10.7 | 10.9 | 10.3 |
| Width mm. | 7.6 | 7.4 | 7.8 |
| Thickness | 3.7 | 4.4 | 4.2 |
| Weight of 1000K gm. | 273.5 | 233.0 | 247.8 |
| Endosperm Type | normal | normal | normal |
| Endosperm Color | yellow | yellow | yellow |

*These are typical values. Values may vary due to environment. Other values that are substantially equivalent are also within the scope of the invention. Substantially equivalent refers to quantitative traits that when compared do not show statistical differences of their means.

V. Single Gene Conversions

When the term inbred corn plant is used in the context of the present invention, this also includes any single gene conversions of that inbred. The term single gene converted plant as used herein refers to those corn plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol (Poehlman and Sleper, 1994; Fehr, 1987). In a typical backcross protocol, the original inbred of interest (recurrent parent) is crossed to a second inbred (nonrecurrent part It) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired morphological and physiological constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Examples of these traits include but are not limited to, male sterility, waxy starch, herbicide resistance, resistance for bacterial, fungal, or viral disease, insect resistance, male fertility, enhanced nutritional quality, and industrial usage. These genes are generally inherited through the nucleus. Some known exceptions to this are the genes for male sterility, some of which are inherited cytoplasmically, but still act as single gene traits. Several of these single gene traits are described in U.S. Ser. No. 07/113,561, filed Aug. 25, 1993, the disclosure of which is specifically hereby incorporated by reference.

Direct selection may be applied where the single gene acts as a dominant trait. An example might be the herbicide resistance trait. For this selection process, the progeny of the initial cross are sprayed with the herbicide prior to the backcrossing. The spraying eliminates any plants which do not have the desired herbicide resistance characteristic, and only those plants which have the herbicide resistance gene are used in the subsequent backcross. This process is then repeated for all additional backcross generations.

The waxy characteristic is an example of a recessive trait. In this example, the progeny resulting from the first backcross generation (BC1) must be grown and selfed. A test is then run on the selfed seed from the BC1 plant to determine which BC1 plants carried the recessive gene for the waxy trait. In other recessive traits, additional progeny testing, for example growing additional generations such as the BC1S1 may be required to determine which plants carry the recessive gene.

VI. Origin and Breeding History of an Exemplary Single Gene Converted Plant

85DGD1 MLms is a single gene conversion of 85DGD1 to cytoplasmic male sterility. 85DGD1 MLms was derived using backcross methods. 85DGD1 (a proprietary inbred of DEKALB Genetics Corporation) was used as the recurrent parent and MLms, a germplasm source carrying ML cytoplasmic sterility, was used as the nonrecurrent parent. The breeding history of the single gene converted inbred 85DGD1 MLms can be summarized as follows:

| | |
|---|---|
| Hawaii Nurseries Planting Date 4-2-92 | Made up S-O: Female row 585 male row 500 |
| Hawaii Nurseries Planting Date 7-15-92 | S-O was grown and plants were backcrossed times 85DGD1 (rows 444 ' 443) |
| Hawaii Nurseries Planting Date 11-18-92 | Bulked seed of the BC1 was grown and backcrossed times 85DGD1 (rows V3-27 ' V3-26) |
| Hawaii Nurseries Planting Date 4-2-93 | Bulked seed of the BC2 was grown and backcrossed times 85DGD1 (rows 37 ' 36) |
| Hawaii Nurseries Planting Date 7-14-93 | Bulked seed of the BC3 was grown and backcrossed times 85DGD1 (rows 99 ' 98) |
| Hawaii Nurseries Planting Date 10-28-93 | Bulked seed of BC4 was grown and backcrossed times 85DGD1 (rows KS-63 ' KS-62) |
| Summer 1994 | A single ear of the BC5 was grown and backcrossed times 85DGD1 |

-continued

| | |
|---|---|
| | (MC94-822 ' MC94-822-7) |
| Winter 1994 | Bulked seed of the BC6 was grown and back-crossed times 85DGD1 (3Q-1 ' 3Q-2) |
| Summer 1995 | Seed of the BC7 was bulked and named 85DGD1 MLms. |
| Hawaii Nurseries Planting Date 4-2-92 | Made up S-O: Female row 585 male row 500 |
| Hawaii Nurseries Planting Date 7-15-92 | S-O was grown and plants were backcrossed times 85DGD1 (rows 444 ' 443) |
| Hawaii Nurseries Planting Date 11-18-92 | Bulked seed of the BC1 was grown and back-crossed times 85DGD1 (rows V3-27 ' V3-26) |
| Hawaii Nurseries Planting Date 4-2-93 | Bulked seed of the BC2 was grown and back-crossed times 85DGD1 (rows 37 ' 36) |
| Hawaii Nurseries Planting Date 7-14-93 | Bulked seed of the BC3 was grown and back-crossed times 85DGD1 (rows 99 ' 98) |

VII. Tissue Culture and in vitro Regeneration of Corn Plants

A further aspect of the invention relates to tissue culture of corn plants designated, separately, 01DIB2 or 01IZB2. As used herein, the term "tissue culture" indicates a composition comprising isolated cells of the same or a different type or a collection of such cells organized into parts of a plant. Exemplary types of tissue cultures are plant protoplast, plant calli, plant clumps, and plant cells that are intact in plants or parts of plants, such as embryos, pollen, flowers, kernels, ears, cobs, leaves, husks, stalks, roots, root tips, anthers, silk and the like. In a preferred embodiment, tissue culture is embryos, protoplast, meristematic cells, pollen, leaves or anthers. Means for preparing and maintaining plant tissue culture are well known in the art. By way of example, a tissue culture comprising organs such as tassels or anthers, has been used to produce regenerated plants. (See, U.S. patent application Ser. Nos. 07/992,637, filed Dec. 18, 1992 and 07/995,938, filed Dec. 21, 1992, now issued as U.S. Pat. No. 5,322,789, issued Jun. 21, 1994, the disclosures of which are incorporated herein by reference).

A. Tassel/Anther Culture

Tassels contain anthers which in turn enclose microspores. Microspores develop into pollen. For anther/microspore culture, if tassels are the plant composition, they are preferably selected at a stage when the microspores are uninucleate, that is, include only one, rather than 2 or 3 nuclei. Methods to determine the correct stage are well known to those skilled in the art and include mitramycin fluorescent staining (Pace et al., 1987), trypan blue (preferred) and acetocarmine squashing. The mid-uninucleate microspore stage has been found to be the developmental stage most responsive to the subsequent methods disclosed to ultimately produce plants.

Although microspore-containing plant organs such as tassels can generally be pretreated at any cold temperature below about 25° C., a range of 4 to 25° C. is preferred, and a range of 8 to 14° C. is particularly preferred. Although other temperatures yield embryoids and regenerated plants, cold temperatures produce optimum response rates compared to pretreatment at temperatures outside the preferred range. Response rate is measured as either the number of embryoids or the number of regenerated plants per number of microspores initiated in culture.

Although not required, when tassels are employed as the plant organ, it is generally preferred to sterilize their surface. Following surface sterilization of the tassels, for example, with a solution of calcium hypochloride, the anthers are removed from about 70 to 150 spikelets (small portions of the tassels) and placed in a preculture or pretreatment medium. Larger or smaller amounts can be used depending on the number of anthers.

When one elects to employ tassels directly, tassels are preferably pretreated at a cold temperature for a predefined time, preferably at 10° C. for about 4 days. After pretreatment of a whole tassel at a cold temperature, dissected anthers are further pretreated in an environment that diverts microspores from their developmental pathway. The function of the preculture medium is to switch the developmental program from one of pollen development to that of embryoid/callus development. An embodiment of such an environment in the form of a preculture medium includes a sugar alcohol, for example mannitol or sorbitol, inositol or the like. An exemplary synergistic combination is the use of mannitol at a temperature of about 10° C. for a period ranging from about 10 to 14 days. In a preferred embodiment, 3 ml of 0.3 M mannitol combined with 50 mg/l of ascorbic acid, silver nitrate and colchicine is used for incubation of anthers at 10° C. for between 10 and 14 days. Another embodiment is to substitute sorbitol for mannitol. The colchicine produces chromosome doubling at this early stage. The chromosome doubling agent is preferably only present at the preculture stage.

It is believed that the mannitol or other similar carbon structure or environmental stress induces starvation and functions to force microspores to focus their energies on entering developmental stages. The cells are unable to use, for example, mannitol as a carbon source at this stage. It is believed that these treatments confuse the cells causing them to develop as embryoids and plants from microspores. Dramatic increases in development from these haploid cells, as high as 25 embryoids in $10^4$ microspores, have resulted from using these methods.

In embodiments where microspores are obtained from anthers, microspores can be released from the anthers into an isolation medium following the mannitol preculture step. One method of release is by disruption of the anthers, for example, by chopping the anthers into pieces with a sharp instrument, such as a razor blade, scalpel or Waring blender. The resulting mixture of released microspores, anther fragments and isolation medium are then passed through a filter to separate microspores from anther wall fragments. An embodiment of a filter is a mesh, more specifically, a nylon mesh of about 112 mm pore size. The filtrate which results from filtering the microspore-containing solution is preferably relatively free of anther fragments, cell walls and other debris.

In a preferred embodiment, isolation of microspores is accomplished at a temperature below about 25° C. and, preferably at a temperature of less than about 15° C. Preferably, the isolation media, dispersing tool (e.g., razor blade) funnels, centrifuge tubes and dispersing container (e.g., petri dish) are all maintained at the reduced temperature during isolation. The use of a precooled dispersing tool to isolate maize microspores has been reported (Gaillard et al., 1991).

Where appropriate and desired, the anther filtrate is then washed several times in isolation medium. The purpose of the washing and centrifugation is to eliminate any toxic compounds which are contained in the non-microspore part of the filtrate and are created by the chopping process. The centrifugation is usually done at decreasing spin speeds, for example, 1000, 750, and finally 500 rpms.

The result of the foregoing steps is the preparation of a relatively pure tissue culture suspension of microspores that are relatively free of debris and anther remnants.

To isolate microspores, an isolation media is preferred. An isolation media is used to separate microspores from the anther walls while maintaining their viability and embryogenic potential. An illustrative embodiment of an isolation media includes a 6 percent sucrose or maltose solution combined with an antioxidant such as 50 mg/l of ascorbic acid, 0.1 mg/l biotin and 400 mg/l of proline, combined with 10 mg/l of nicotinic acid and 0.5 mg/l $AgNO_3$. In another embodiment, the biotin and proline are omitted.

An isolation media preferably has a higher antioxidant level where used to isolate microspores from a donor plant (a plant from which a plant composition containing a microspore is obtained) that is field grown in contrast to greenhouse grown. A preferred level of ascorbic acid in an isolation medium is from about 50 mg/l to about 125 mg/l and, more preferably from about 50 mg/l to about 100 mg/l.

One can find particular benefit in employing a support for the microspores during culturing and subculturing. Any support that maintains the cells near the surface can be used. The microspore suspension is layered onto a support, for example by pipetting. There are several types of supports which are suitable and are within the scope of the invention. An illustrative embodiment of a solid support is a TRANSWELL® culture dish. Another embodiment of a solid support for development of the microspores is a bilayer plate wherein liquid media is on top of a solid base. Other embodiments include a mesh or a millipore filter. Preferably, a solid support is a nylon mesh in the shape of a raft. A raft is defined as an approximately circular support material which is capable of floating slightly above the bottom of a tissue culture vessel, for example, a petri dish, of about a 60 or 100 mm size, although any other laboratory tissue culture vessel will suffice. In an illustrative embodiment, a raft is about 55 mm in diameter.

Culturing isolated microspores on a solid support, for example, on a 10 mm pore nylon raft floating on 2.2 ml of medium in a 60 mm petri dish, prevents microspores from sinking into the liquid medium and thus avoiding low oxygen tension. These types of cell supports enable the serial transfer of the nylon raft with its associated microspore/embryoids ultimately to full strength medium containing activated charcoal and solidified with, for example, GELRITE™ (solidifying agent). The charcoal is believed to absorb toxic wastes and intermediaries. The solid medium allows embryoids to mature.

The liquid medium passes through the mesh while the microspores are retained and supported at the medium-air interface. The surface tension of the liquid medium in the petri dish causes the raft to float. The liquid is able to pass through the mesh: consequently, the microspores stay on top. The mesh remains on top of the total volume of liquid medium. An advantage of the raft is to permit diffusion of nutrients to the microspores. Use of a raft also permits transfer of the microspores from dish to dish during subsequent subculture with minimal loss, disruption or disturbance of the induced embryoids that are developing. The rafts represent an advantage over the multi-welled TRANSWELL® plates, which are commercially available from COSTAR, in that the commercial plates are expensive. Another disadvantage of these plates is that to achieve the serial transfer of microspores to subsequent media, the membrane support with cells must be peeled off the insert in the wells. This procedure does not produce as good a yield nor as efficient transfers, as when a mesh is used as a vehicle for cell transfer.

The culture vessels can be further defined as either (1) a bilayer 60 mm petri plate wherein the bottom 2 ml of medium are solidified with 0.7 percent agarose overlaid with 1 mm of liquid containing the microspores; (2) a nylon mesh raft wherein a wafer of nylon is floated on 1.2 ml of medium and 1 ml of isolated microspores is pipetted on top; or (3) TRANSWELL® plates wherein isolated microspores are pipetted onto membrane inserts which support the microspores at the surface of 2 ml of medium.

After the microspores have been isolated, they are cultured in a low strength anther culture medium until about the 50 cell stage when they are subcultured onto an embryoid/callus maturation medium. Medium is defined at this stage as any combination of nutrients that permit the microspores to develop into embryoids or callus. Many examples of suitable embryoid/callus promoting media are well known to those skilled in the art. These media will typically comprise mineral salts, a carbon source, vitamins, growth regulations. A solidifying agent is optional. A preferred embodiment of such a media is referred to by the inventor as the "D medium" which typically includes 6N1 salts, $AgNO_3$ and sucrose or maltose.

In an illustrative embodiment, 1 ml of isolated microspores are pipetted onto a 10 mm nylon raft and the raft is floated on 1.2 ml of medium "D", containing sucrose or, preferably maltose. Both calli and embryoids can develop. Calli are undifferentiated aggregates of cells. Type I is a relatively compact, organized and slow growing callus. Type II is a soft, friable and fast-growing one. Embryoids are aggregates exhibiting some embryo-like structures. The embryoids are preferred for subsequent steps to regenerating plants. Culture medium "D" is an embodiment of medium that follows the isolation medium and replaces it. Medium "D" promotes growth to an embryoid/callus. This medium comprises 6N1 salts at ⅛ the strength of a basic stock solution, (major components) and minor components, plus 12 percent sucrose or, preferably 12 percent maltose, 0.1 mg/l B1, 0.5 mg/l nicotinic acid, 400 mg/l proline and 0.5 mg/l silver nitrate. Silver nitrate is believed to act as an inhibitor to the action of ethylene. Multi-cellular structures of approximately 50 cells each generally arise during a period of 12 days to 3 weeks. Serial transfer after a two week incubation period is preferred.

After the petri dish has been incubated for an appropriate period of time, preferably two weeks, in the dark at a predefined temperature, a raft bearing the dividing microspores is transferred serially to solid based media which promotes embryo maturation. In an illustrative embodiment, the incubation temperature is 30° C. and the mesh raft supporting the embryoids is transferred to a 100 mm petri dish containing the 6N1-TGR-4P medium, an "anther culture medium." This medium contains 6N1 salts, supplemented with 0.1 mg/l TIBA, 12 percent sugar (sucrose, maltose or a combination thereof), 0.5 percent activated charcoal, 400 mg/l proline, 0.5 mg/l B, 0.5 mg/l nicotinic acid, and 0.2 percent GELRITE™ (solidifying agent) and is capable of promoting the maturation of the embryoids. Higher quality embryoids, that is, embryoids which exhibit more organized development, such as better shoot meristem formation without precocious germination were typically obtained with the transfer to full strength medium compared to those resulting from continuous culture using only, for example, the isolated microspore culture (IMC) Medium "D." The maturation process permits the pollen embryoids to develop further in route toward the eventual regeneration of plants. Serial transfer occurs to full strength solidified 6N1 medium using either the nylon raft the TRANSWELL® membrane or bilayer plates, each one requiring the movement of developing embryoids to permit further development into physiologically more mature structures.

In an especially preferred embodiment, microspores are isolated in an isolation media comprising about 6 percent maltose, cultured for about two weeks in an embryoid/calli induction medium comprising about 12 percent maltose and then transferred to a solid medium comprising about 12 percent sucrose.

At the point of transfer of the raft after about two weeks incubation, embryoids exist on a nylon support. The purpose of transferring the raft with the embryoids to a solidified medium after the incubation is to facilitate embryo maturation. Mature embryoids at this point are selected by visual inspection indicated by zygotic embryo-like dimensions and structures and are transferred to the shoot initiation medium. It is preferred that shoots develop before roots, or that shoots and roots develop concurrently. If roots develop before shoots, plant regeneration can be impaired. To produce solidified media, the bottom of a petri dish of approximately 100 mm is covered with about 30 ml of 0.2 percent GEL-RITE™ (solidifying agent) solidified medium. A sequence of regeneration media are used for whole plant formation from the embryoids.

During the regeneration process, individual embryoids are induced to form plantlets. The number of different media in the sequence can vary depending on the specific protocol used. Finally, a rooting medium is used as a prelude to transplanting to soil. When plantlets reach a height of about 5 cm, they are then transferred to pots for further growth into flowering plants in a greenhouse by methods well known to those skilled in the art.

Plants have been produced from isolated microspore cultures by methods disclosed herein, including self-pollinated plants. The rate of embryoid induction was much higher with the synergistic preculture treatment consisting of a combination of stress factors, including a carbon source which can be capable of inducing starvation, a cold temperature and colchicine, than has previously been reported. An illustrative embodiment of the synergistic combination of treatments leading to the dramatically improved response rate compared to prior methods, is a temperature of about 10° C., mannitol as a carbon source, and 0.05 percent colchicine.

The inclusion of ascorbic acid, an anti-oxidant, in the isolation medium is preferred for maintaining good microspore viability. However, there seems to be no advantage to including mineral salts in the isolation medium. The osmotic potential of the isolation medium was maintained optimally with about 6 percent sucrose, although a range of 2 percent to 12 percent is within the scope of this invention.

In an embodiment of the embryoid/callus organizing media, mineral salts concentration in IMC Culture Media "D" is (⅛×), the concentration which is used also in anther culture medium. The 6N1 salts major components have been modified to remove ammonium nitrogen. Osmotic potential in the culture medium is maintained with about 12 percent sucrose and about 400 mg/l proline. Silver nitrate (0.5 mg/l) was included in the medium to modify ethylene activity. The preculture media is further characterized by having a pH of about 5.7 to 6.0. Silver nitrate and vitamins do not appear to be crucial to this medium but do improve the efficiency of the response.

Whole anther cultures can also be used in the production of monocotyledonous plants from a plant culture system. There are some basic similarities of anther culture methods and microspore culture methods with regard to the media used. A difference from isolated microspore cultures is that undisrupted anthers are cultured, so that a support, e.g., a nylon mesh support, is not needed. The first step in developing the anther cultures is to incubate tassels at a cold temperature. A cold temperature is defined as less than about 25° C. More specifically, the incubation of the tassels is preferably performed at about 10° C. A range of 8 to 14° C. is also within the scope of the invention. The anthers are then dissected from the tassels, preferably after surface sterilization using forceps, and placed on solidified medium. An example of such a medium is designated by the inventors as 6N1-TGR-P4.

The anthers are then treated with environmental conditions that are combinations of stresses that are capable of diverting microspores from gametogenesis to embryogenesis. It is believed that the stress effect of sugar alcohols in the preculture medium, for example, mannitol, is produced by inducing starvation at the predefined temperature. In one embodiment, the incubation pretreatment is for about 14 days at 10° C. It was found that treating the anthers in addition with a carbon structure, an illustrative embodiment being a sugar alcohol, preferably, mannitol, produces dramatically higher anther culture response rates as measured by the number of eventually regenerated plants, than by treatment with either cold treatment or mannitol alone. These results are particularly surprising in light of teachings that cold is better than mannitol for these purposes, and that warmer temperatures interact with mannitol better.

To incubate the anthers, they are floated on a preculture medium which diverts the microspores from gametogenesis, preferably on a mannitol carbon structure, more specifically, 0.3 M of mannitol plus 50 mg/l of ascorbic acid. 3 ml is about the total amount in a dish, for example, a tissue culture dish, more specifically, a 60 mm petri dish. Anthers are isolated from about 120 spikelets for one dish yields about 360 anthers.

Chromosome doubling agents can be used in the preculture media for anther cultures. Several techniques for doubling chromosome number (Jensen, 1974; Wan et al., 1989) have been described. Colchicine is one of the doubling agents. However, developmental abnormalities arising from in vitro cloning are further enhanced by colchicine treatments, and previous reports indicated that colchicine is toxic to microspores. The addition of colchicine in increasing concentrations during mannitol pretreatment prior to anther culture and microspore culture has achieved improved percentages.

An illustrative embodiment of the combination of a chromosome doubling agent and preculture medium is one which contains colchicine. In a specific embodiment, the colchicine level is preferably about 0.05 percent. The anthers remain in the mannitol preculture medium with the additives for about 10 days at 10° C. Anthers are then placed on maturation media, for example, that designated 6N1-TGR-P4, for 3 to 6 weeks to induce embryoids. If the plants are to be regenerated from the embryoids, shoot regeneration medium is employed, as in the isolated microspore procedure described in the previous sections. Other regeneration media can be used sequentially to complete regeneration of whole plants.

The anthers are then exposed to embryoid/callus promoting medium, for example, that designated 6N1-TGR-P4 to obtain callus or embryoids. The embryoids are recognized by identification visually of embryonic-like structures. At this stage, the embryoids are transferred serially to a series of regeneration media In an illustrative embodiment, the shoot initiation medium comprises BAP (6-benzyl-aminopurine) and NAA (naphthalene acetic acid). Regeneration protocols for isolated microspore cultures and anther cultures are similar.

B. Other Cultures and Regeneration

The present invention contemplates a corn plant regenerated from a tissue culture of an inbred (e.g., 01DIB2 or 01IZB2) or hybrid plant (2003929) of the present invention. As is well known in the art, tissue culture of corn can be used for the in vitro regeneration of a corn plant. By way of example, a process of tissue culturing and regeneration of corn is described in European Patent Application, publication 160,390, the disclosure of which is incorporated by reference. Corn tissue culture procedures are also described in Green and Rhodes (1982) and Duncan et al., (1985). The study by Duncan indicates that 97 percent of cultured plants produced calli capable of regenerating plants. Subsequent studies have shown that both inbreds and hybrids produced 91 percent regenerable calli that produced plants.

Other studies indicate that non-traditional tissues are capable of producing somatic embryogenesis and plant regeneration. See, e.g., Songstad et al. (1988); Conger et al. (1987); and Rao et al., (1986), the disclosures of which are incorporated herein by reference.

Briefly, by way of example, to regenerate a plant of this invention, cells are selected following growth in culture. Where employed, cultured cells are preferably grown either on solid supports or in the form of liquid suspensions as set forth above. In either instance, nutrients are provided to the cells in the form of media, and environmental conditions are controlled. There are many types of tissue culture media comprising amino acids, salts, sugars, hormones and vitamins. Most of the media employed to regenerate inbred and hybrid plants have some similar components, the media differ in the composition and proportions of their ingredients depending on the particular application envisioned. For example, various cell types usually grow in more than one type of media, but exhibit different growth rates and different morphologies, depending on the growth media. In some media, cells survive but do not divide. Various types of media suitable for culture of plant cells have been previously described and discussed above.

An exemplary embodiment for culturing recipient corn cells in suspension cultures includes using embryogenic cells in Type II (Armstrong and Green, 1985; Gordon-Kamm et al., 1990) callus, selecting for small (10 to 30 m) isodiametric, cytoplasmically dense cells, growing the cells in suspension cultures with hormone containing media, subculturing into a progression of media to facilitate development of shoots and roots, and finally, hardening the plant and readying it metabolically for growth in soil.

Meristematic cells (i.e., plant cells capable of continual cell division and characterized by an undifferentiated cytological appearance, normally found at growing points or tissues in plants such as root tips, stem apices, lateral buds, etc.) can be cultured.

Embryogenic calli are produced (Gordon-Kamm et al., 1990). Specifically, plants from hybrids produced from crossing an inbred of the present invention with another inbred are grown to flowering in a greenhouse. Explants from at least one of the following $F_1$ tissues: the immature tassel tissue, intercalary meristems and leaf bases, apical meristems, and immature ears are placed in an initiation medium which contain MS salts, supplemented with thiamine, agar, and sucrose. Cultures are incubated in the dark at about 23° C. All culture manipulations and selections are performed with the aid of a dissecting microscope.

After about 5 to 7 days, cellular outgrowths are observed from the surface of the explants. After about 7 to 21 days, the outgrowths are subcultured by placing them into fresh medium of the same composition. Some of the intact immature embryo explants are placed on fresh medium. Several subcultures later (after about 2 to 3 months) enough material is present from explants for subdivision of these embryogenic calli into two or more pieces.

Callus pieces from different explants are not mixed. After further growth and subculture (about 6 months after embryogenic callus initiation), there are usually between 1 and 100 pieces derived ultimately from each selected explant. During this time of culture expansion, a characteristic embryogenic culture morphology develops as a result of careful selection at each subculture. Any organized structures resembling roots or root primordia are discarded. Material known from experience to lack the capacity for sustained growth is also discarded (translucent, watery, embryogenic structures). Structures with a firm consistency resembling at least in part the scutulum of the in vivo embryo are selected.

The callus is maintained on agar-solidified MS-type media A preferred hormone is 2,4-D. Visual selection of embryo-like structures is done to obtain subcultures. Transfer of material other than that displaying embryogenic morphology results in loss of the ability to recover whole plants from the callus.

Cell suspensions are prepared from the calli by selecting cell populations that appear homogeneous macroscopically. A portion of the friable, rapidly growing embryogenic calli is inoculated into MS Medium. The calli in medium are incubated at about 27° C. on a gyrotary shaker in the dark or in the presence of low light. The resultant suspension culture is transferred about once every seven days by taking about 5 to 10 ml of the culture and introducing this inoculum into fresh medium of the composition listed above.

For regeneration, embryos which appear on the callus surface are selected and regenerated into whole plants by transferring the embryogenic structures into a sequence of solidified media which include decreasing concentrations of 2,4-D or other auxins. Other hormones which can be used in the media include dicamba, NAA, ABA, BAP, and 2-NCA. The reduction is relative to the concentration used in culture maintenance media. Plantlets are regenerated from these embryos by transfer to a hormone-free medium, subsequently transferred to soil, and grown to maturity.

Progeny are produced by taking pollen and selfing, backcrossing or sibling regenerated plants by methods well known to those skilled in the arts. Seeds are collected from the regenerated plants.

VIII. Processes of Preparing Corn Plants and the Corn Plants Produced by Such Processes The present invention also provides a process of preparing a novel corn plant and a corn plant produced by such a process. In accordance with such a process, a first parent corn plant is crossed with a second parent corn plant wherein at least one of the first and second corn plants is the inbred corn plant 01DIB2 or 01IZB2. In one embodiment, a corn plant prepared by such a process is a first generation $F_1$ hybrid corn plant prepared by a process wherein both the first and second parent corn plants are inbred corn plants.

Corn plants (*Zea mays L.*) can be crossed by either natural or mechanical techniques. Natural pollination occurs in corn when wind blows pollen from the tassels to the silks that protrude from the tops of the incipient ears. Mechanical pollination can be effected either by controlling the types of pollen that can blow onto the silks or by pollinating by hand.

In a preferred embodiment, crossing comprises the steps of:

(a) planting in pollinating proximity seeds of a first and a second parent corn plant, and preferably, seeds of a first inbred corn plant and a second, distinct inbred corn plant;

(b) cultivating or growing the seeds of the first and second parent corn plants into plants that bear flowers;

(c) emasculating flowers of either the first or second parent corn plant, i.e., treating the flowers so as to prevent pollen production, in order to produce an emasculated parent corn plant;

(d) allowing natural cross-pollination to occur between the first and second parent corn plant;

(e) harvesting seeds produced on the emasculated parent corn plant; and, where desired, and (f) growing the harvested seed into a corn plant, or preferably, a hybrid corn plant.

Parental plants are planted in pollinating proximity to each other by planting the parental plants in alternating rows, in blocks or in any other convenient planting pattern. Plants of both parental parents are cultivated and allowed to grow until the time of flowering. Advantageously, during this growth stage, plants are in general treated with fertilizer and/or other agricultural chemicals as considered appropriate by the grower.

At the time of flowering, in the event that plant 01DIB2 or 01IZB2, is employed as the male parent, the tassels of the other parental plant are removed from all plants employed as the female parental plant. The detasseling can be achieved manually but also can be done by machine if desired.

The plants are then allowed to continue to grow and natural cross-pollination occurs as a result of the action of wind, which is normal in the pollination of grasses, including corn. As a result of the emasculation of the female parent plant, all the pollen from the male parent plant, e.g., 01DIB2 or 01IZB2, is available for pollination because tassels, and thereby pollen bearing flowering parts, have been previously removed from all plants of the inbred plant being used as the female in the hybridization. Of course, during this hybridization procedure, the parental varieties are grown such that they are isolated from other corn fields to prevent any accidental contamination of pollen from foreign sources. These isolation techniques are well within the skill of those skilled in this art.

Both of the parent inbred plants of corn are allowed to continue to grow until maturity, but only the ears from the female inbred parental plants are harvested to obtain seeds of a novel $F_1$ hybrid. The novel $F_1$ hybrid seed produced can then be planted in a subsequent growing season with the desirable characteristics in terms of $F_1$ hybrid corn plants providing improved grain yields and the other desirable characteristics disclosed herein, being achieved.

Alternatively, in another embodiment, both first and second parent corn plants can come from the same inbred corn plant, i.e., from the inbreds designated, separately, 01DIB2 or 01IZB2. Thus, any corn plant produced using a process of the present invention and inbred corn plant 01DIB2 or 01IZB2, is contemplated by this invention. As used herein, crossing can mean selfing, backcrossing, crossing to another or the same inbred, crossing to populations, and the like. All corn plants produced using the present inbred corn plants, i.e., 01DIB2 or 01IZB2, as a parent are within the scope of this invention.

The utility of the inbred plants 01DIB2 and 01IZB2, also extends to crosses with other species. Commonly, suitable species will be of the family Graminaceae, and especially of the genera Zea, Tripsacum, Coix, Schierachne, Polytoca, Chionachne, and Trilobachne, of the tribe Maydeae. Of these, Zea and Tripsacum, are most preferred. Potentially suitable for crosses with 01DIB2 and 01IZB2 can be the various varieties of grain sorghum, *Sorghum bicolor* (L.) Moench.

A. $F_1$ Hybrid Corn Plant and Seed Production

Where the inbred corn plant 01DIB2 or 01IZB2 is crossed with another, different, corn inbred, a first generation ($F_1$) corn hybrid plant is produced. Both a $F_1$ hybrid corn plant and a seed of that $F_1$ hybrid corn plant are contemplated as aspects of the present invention.

Inbreds 01DIB2 and 01IZB2 have been used to prepare an $F_1$ hybrid corn plant, designated 2003929.

The goal of a process of producing an $F_1$ hybrid is to manipulate the genetic complement of corn to generate new combinations of genes which interact to yield new or improved traits (phenotypic characteristics). A process of producing an $F_1$ hybrid typically begins with the production of one or more inbred plants. Those plants are produced by repeated crossing of ancestrally related corn plants to try and concentrate certain genes within the inbred plants. The production of inbred 2003929 has been set forth hereinbefore.

Corn has a diploid phase which means two conditions of a gene (two alleles) occupy each locus (position on a chromosome). If the alleles are the same at a locus, there is said to be homozygosity. If they are different, there is said to be heterozygosity. In a completely inbred plant, all loci are homozygous. Because many loci when homozygous are deleterious to the plant, in particular leading to reduced vigor, less kernels, weak and/or poor growth, production of inbred plants is an unpredictable and arduous process. Under some conditions, heterozygous advantage at some loci effectively bars perpetuation of homozygosity.

Inbreeding requires coddling and sophisticated manipulation by human breeders. Even in the extremely unlikely event inbreeding rather than crossbreeding occurred in natural corn, achievement of complete inbreeding cannot be expected in nature due to well known deleterious effects of homozygosity and the large number of generations the plant would have to breed in isolation. The reason for the breeder to create inbred plants is to have a known reservoir of genes whose gametic transmission is at least somewhat predictable.

The development of inbred plants generally requires at least about 5 to 7 generations of selfing. Inbred plants are then cross-bred in an attempt to develop improved $F_1$ hybrids. Hybrids are then screened and evaluated in small scale field trials. Typically, about 10 to 15 phenotypic traits, selected for their potential commercial value, are measured. A selection index of the most commercially important traits is used to help evaluate hybrids. FACT, an acronym for Field Analysis Comparison Trial (strip trials), is an on-farm testing program employed by DEKALB Plant Genetics to perform the final evaluation of the commercial potential of a product.

During the next several years, a progressive elimination of hybrids occurs based on more detailed evaluation of their phenotype. Eventually, strip trials (FACT) are conducted to formally compare the experimental hybrids being developed with other hybrids, some of which were previously developed and generally are commercially successful. That is, comparisons of experimental hybrids are made to competitive hybrids to determine if there was any advantage to further commercial development of the experimental hybrids. Examples of such comparisons are presented in Section B, hereinbelow.

When the inbred parental plant, i.e., 01DIB2 or 01IZB2, is crossed with another inbred plant to yield a hybrid (such as the hybrid 2003929), the original inbred can serve as either the maternal or paternal plant. For many crosses, the outcome is the same regardless of the assigned sex of the parental plants.

However, there is often one of the parental plants that is preferred as the maternal plant because of increased seed yield and production characteristics. Some plants produce tighter ear husks leading to more loss, for example due to rot. There can be delays in silk formation which deleteriously affect timing of the reproductive cycle for a pair of parental inbreds. Seed coat characteristics can be preferable in one plant. Pollen can be shed better by one plant. Other variables can also affect preferred sexual assignment of a particular cross.

B. $F_1$ Hybrid Comparisons

As mentioned in Section A, hybrids are progressively eliminated following detailed evaluations of their phenotype, including formal comparisons with other commercially successful hybrids. Strip trials are used to compare the phenotypes of hybrids grown in as many environments as possible. They are performed in many environments to assess overall performance of the new hybrids and to select optimum growing conditions. Because the corn is grown in close proximity, environmental factors that affect gene expression, such as moisture, temperature, sunlight and pests, are minimized. For a decision to be made that a hybrid is worth making commercially available, it is not necessary that the hybrid be better than all other hybrids. Rather, significant improvements must be shown in at least some traits that would create improvements in some niches.

Examples of such comparative data are set forth hereinbelow in Table 7, which presents a comparison of performance data for the hybrid 2003929, versus several other selected hybrids of commercial value.

Specifically, Table 7 presents a comparison of performance data for 2003929 versus two selected hybrids of commercial value (DK442 and DK471). 2003929 has both 01DIB2 and 01IZB2, inbreds of the invention, as inbred parents.

TABLE 7

COMPARATIVE DATA FOR 2003929

| HYBRID | NTEST | SI % C | YLD BU | MST PTS | STL % | RTL % | DRP % | FLSTD % M | SV RAT | ELSTD % M | PHT INCH | EHT INCH | BAR % | SG RAT | TST LBS | FGDU | ESTR DAYS |
|---|---|---|---|---|---|---|---|---|---|---|---|---|---|---|---|---|---|
| 2003929 | R 201 | 102.6 | 147.0 | 19.4 | 3.9 | 1.6 | 0.0 | 100.8 | 5.6 | 103.8 | 85.7 | 40.9 | | 4.0 | 54.6 | 1281 | 94.2 |
| DK442 | | 98.1 | 145.6 | 19.7 | 7.1 | 1.9 | 0.2 | 100.7 | 5.6 | 102.3 | 88.9 | 44.3 | | 5.8 | 53.6 | 1289 | 94.5 |
| DEV | | 4.5 | 1.4 | −0.3 | −3.2 | −0.3 | −0.1 | 0.0 | 0.1 | 1.5 | −3.2 | −3.4 | | −1.8 | 1.0 | −8.3 | −0.3 |
| | | ** | | | ** | ** | * | | | ** | ** | ** | | ** | ** | + | * |
| 2003929 | F 73 | 108.9 | 136.1 | 18.0 | 5.1 | 1.1 | 0.4 | 102.8 | | | | | | | 54.5 | | 94.1 |
| DK442 | | 103.4 | 134.9 | 18.6 | 9.9 | 0.5 | 1.0 | 98.7 | | | | | | | 53.5 | | 95.3 |
| DEV | | 5.5 | 1.2 | −0.6 | −4.8 | 0.7 | −0.5 | 4.1 | | | | | | | 1.0 | | −1.2 |
| | | ** | | ** | ** | + | ** | ** | | | | | | | ** | | ** |
| 2003929 | R 201 | 102.6 | 147.0 | 19.4 | 3.9 | 1.6 | 0.0 | 100.8 | 5.6 | 103.8 | 85.7 | 40.9 | | 4.0 | 54.5 | 1282 | 94.2 |
| DK471 | | 107.2 | 154.8 | 20.4 | 4.8 | 2.6 | 0.2 | 100.6 | 5.2 | 102.3 | 88.8 | 42.9 | | 5.6 | 53.2 | 1309 | 95.7 |
| DEV | | −4.6 | −7.8 | −1.0 | −0.9 | −1.0 | −0.1 | 0.1 | 0.4 | 1.5 | −3.0 | −2.0 | | −1.6 | 1.3 | −27.0 | −1.5 |
| | | ** | ** | ** | ** | * | ** | | ** | * | ** | ** | | ** | ** | ** | ** |
| 2003929 | F 94 | 107.8 | 136.2 | 17.5 | 6.2 | 0.9 | 0.4 | 102.9 | | | | | | | 54.9 | | 94.6 |
| DK471 | | 110.8 | 141.2 | 18.2 | 6.8 | 0.9 | 0.5 | 10.23 | | | | | | | 53.8 | | 96.0 |
| DEV | | −3.0 | −4.9 | −0.7 | −0.6 | −0.0 | −0.2 | 0.6 | | | | | | | 1.2 | | −1.4 |
| | | ** | ** | ** | | | | | | | | | | | ** | | *** |

Significance levels are indicated as: + = 10 percent, * = 5 percent, ** = 1 percent.

LEGEND ABBREVIATIONS:
HYBRID = Hybrid
TEST = Research/FACT
SI % C = Selection Index (percent of check)
YLD BU = Yield (bushels/acre)
MST PTS = Moisture
STL % = Stalk Lodging (percent)
RTL % = Root Lodging (percent)
DRP % = Dropped Ears (percent)
FLSTD % M = Final Stand (percent of test mean)
SV RAT = Seedling Vigor Rating
ELSTD % M = Early Stand (percent of test mean)
PHT INCH = Plant Height (inches)
EHT INCH = Ear Height (inches)
BAR % = Barren Plants (percent)
SG RAT = Staygreen Rating
TST LBS = Test Weight (pounds)
FGDU = GDUs to Shed
ESTR DAYS = Estimated Relative Maturity (days)

As can be seen in Table 7, the hybrid 2003929 has a significant improvement in plant health as exemplified by differences in stay green rating, seedling vigor rating, and percent of stalk lodging when compared to several successful commercial hybrids. This hybrid was developed for improved adaptation to the Eastern Corn Belt. Significant differences are also shown in Table 7 for many other traits.

C. Physical Description of $F_1$ Hybrids

The present invention also provides $F_1$ hybrid corn plants derived from the corn plants 01DIB2 and 01IZB2. Physical characteristics of exemplary hybrids are set forth in Table 8. An explanation of terms used in Table 8 can be found in the Definitions, set forth hereinabove.

Table 8 concerns 2003929, which has both 01DIB2 and 01IZB2 as inbred parents.

TABLE 8

MORPHOLOGICAL TRAITS FOR THE 2003929 PHENOTYPE
YEAR OF DATA: 1994, 1995

| CHARACTERISTIC | VALUE |
|---|---|
| 1. STALK | |
| Diameter (width) cm. | 2.3 |
| Anthocyanin | absent |
| Nodes With Brace Roots | 1.0 |
| Brace Root Color | green |
| Internode Direction | straight |
| Internode Length cm. | 16.3 |
| 2. LEAF | |
| Length cm. | 84.8 |
| Width cm. | 9.7 |
| Marginal Waves | few |
| Longitudinal Creases | few |

TABLE 8-continued

MORPHOLOGICAL TRAITS FOR THE 2003929 PHENOTYPE
YEAR OF DATA: 1994, 1995

| CHARACTERISTIC | VALUE |
|---|---|
| 3. TASSEL | |
| Attitude | open |
| Length cm. | 33.7 |
| Spike Length cm. | 22.7 |
| Peduncle Length cm. | 13.3 |
| Branch Number | 11.4 |
| Anther Color | red |
| Glume Color | green |
| Glume Band | absent |
| 4. EAR | |
| Number Per Stalk | 1.0 |
| Position (attitude) | upright |
| Length cm. | 17.1 |
| Shape | semi-conical |
| Diameter cm. | 4.3 |
| Weight gm. | 177.3 |
| Shank Length cm. | 16.9 |
| Husk Bract | short |
| Husk Cover cm. | 3.5 |
| Husk Color Fresh | green |
| Husk Color Dry | buff |
| Cob Diameter cm. | 2.1 |
| Cob Color | red |
| Shelling Percent | 86.7 |
| 5. KERNEL | |
| Row Number | 13.6 |
| Number Per Row | 35.9 |
| Row Direction | curved |
| Type | dent |
| Cap Color | yellow |
| Side Color | orange |

TABLE 8-continued

MORPHOLOGICAL TRAITS FOR
THE 2003929 PHENOTYPE
YEAR OF DATA: 1994, 1995

| CHARACTERISTIC | VALUE |
|---|---|
| Length (depth) mm. | 12.2 |
| Width mm. | 8.8 |
| Thickness | 3.8 |
| Weight of 1000K gm. | 319.0 |
| Endosperm Type | normal |
| Endosperm Color | yellow |

*These are typical values. Values may vary due to environment. Other values that are substantially equivalent are also within the scope of the invention. Substantially equivalent refers to quantitative traits that when compared do not show statistical differences of their means.

IX. Genetic Complements

In another aspect, the present invention provides a genetic complement of a plant of this invention. In one embodiment, therefore, the present invention contemplates an inbred genetic complement of the inbred corn plants designated, separately, 01DIB2 and 01IZB2. In another embodiment, the present invention contemplates a hybrid genetic complement formed by the combination of a haploid genetic complement from 01DIB2 or 01IZB2 and another haploid genetic complement. Means for determining a genetic complement are well-known in the art.

As used herein, the phrase "genetic complement" means an aggregate of nucleotide sequences, the expression of which sequences defines the phenotype of a corn plant or a cell or tissue of that plant. By way of example, a corn plant is genotyped to determine the array of the inherited markers it possesses. Markers are alleles at a single locus. They are preferably inherited in codominant fashion so that the presence of both alleles at a diploid locus is readily detectable, and they are free of environmental variation, i.e., their heritability is 1. This genotyping is preferably performed on at least one generation of the descendant plant for which the numerical value of the quantitative trait or traits of interest are also determined. The array of single locus genotypes is expressed as a profile of marker alleles, two at each locus. The marker allelic composition of each locus can be either homozygous or heterozygous. Homozygosity is a condition where both alleles at a locus are characterized by the same nucleotide sequence. Heterozygosity refers to different conditions of the gene at a locus. Markers that are used for purposes of this invention include restriction fragment length polymorphisms (RFLPs) and isozymes.

A plant genetic complement can be defined by a genetic marker profiles that can be considered "fingerprints" of a genetic complement. For purposes of this invention, markers are preferably distributed evenly throughout the genome to increase the likelihood they will be near a quantitative trait loci (QTL) of interest (e.g., in tomatoes, Nienhuis et al., 1987). These profiles are partial projections of a sample of genes. One of the uses of markers in general is to exclude, or alternatively include, potential parents as contributing to offspring.

Phenotypic traits characteristic of the expression of a genetic complement of this invention are distinguishable by electrophoretic separation of DNA sequences cleaved by various restriction endonucleases. Those traits (genetic markers) are termed RFLP (restriction fragment length polymorphisms).

Restriction fragment length polymorphisms (RFLPs) are genetic differences detectable by DNA fragment lengths, typically revealed by agarose gel electrophoresis, after restriction endonuclease digestion of DNA. There are large numbers of restriction endonucleases available, characterized by their nucleotide cleavage sites and their source, e.g., EcoRI. Variations in RFLPs result from nucleotide base pair differences which alter the cleavage sites of the restriction endonucleases, yielding different sized fragments.

Means for performing RFLP analyses are well known in the art. Restriction fragment length polymorphism analyses reported herein were conducted by Linkage Genetics. This service is available to the public on a contractual basis. Probes were prepared to the fragment sequences, these probes being complementary to the sequences thereby being capable of hybridizing to them under appropriate conditions well known to those skilled in the art. These probes were label-d with radioactive isotopes or fluorescent dyes for ease of detection. After the fragments were separated by size, they were identified by the probes. Hybridization with a unique cloned sequence permits the identification of a specific chromosomal region (locus). Because all alleles at a locus are detectable, RFLPs are codominant alleles, thereby satisfying a criteria for a genetic marker. They differ from some other types of markers, e.g., from isozymes, in that they reflect the primary DNA sequence, they are not products of transcription or translation. Furthermore, different RFLP genetic marker profiles result from different arrays of restriction endonucleases.

The RFLP genetic marker profile of each of the parental inbreds and exemplary resultant hybrids were determined. Because an inbred is essentially homozygous at all relevant loci, an inbred should, in almost all cases, have only one allele at each locus. In contrast, a diploid genetic marker profile of a hybrid should be the sum of those parents, e.g., if one inbred parent had the allele A at a particular locus, and the other inbred parent had B, the hybrid is AB by inference.

RFLP genetic marker profiles of 01DIB2 and 01IZB2, are presented in Tables 9 and 10.

TABLE 9

RFLP PROFILE OF 01DIB2

| PROBE/ENZYME COMBINATION | 01DIB2 | 2FACC | 91BMA2 |
|---|---|---|---|
| M0264H | G | G | L |
| M0306H | A | A | E |
| M0445E | B | B | B |
| M1234H | D | D | E |
| M1236H | A | A | A |
| M1238H | A | A | A |
| M1406H | A | — | B |
| M1B725E | H | B | — |
| M2239H | D | A | — |
| M2402H | E | E | E |
| M3212S | A | A | A |
| M3247E | B | B | B |
| M3257S | B | B | — |
| M3296H | A | A | D |
| M3432H | H | I | — |
| M3446S | B | B | F |
| M3457E | E | E | E |
| M4386H | B | B | B |
| M4396E | H | H | F |
| M4UMC19H | A | A | A |
| M4UMC31E | C | C | — |
| M4UMC31S | A | A | B |
| M5213S | A | A | B |
| M5288S | A | A | A |
| M5408H | A | A | A |
| M6223E | A | C | — |
| M6280H | E | E | A |
| M6373E | A | E | A |
| M7263E | C | C | A |
| M7391H | C | C | A |
| M7392S | B | C | B |
| M7455H | A | A | C |
| M8110S | B | C | D |

TABLE 9-continued

RFLP PROFILE OF 01DIB2

| PROBE/ENZYME COMBINATION | 01DIB2 | 2FACC | 91BMA2 |
|---|---|---|---|
| M8114E | B | B | E |
| M8268H | B | B | B |
| M8585H | B | A | B |
| M8B2369S | B | D | D |
| M9209E | C | C | A |
| M9211E | C | C | — |
| M9266S | A | A | — |
| M6UMC85H | A | A | — |
| M9B713S | A | A | B |
| M9UMC94H | E | E | — |
| M3UM121X | C | C | — |
| M0UMC130 | H | H | — |

*Probes used to detect RFLPs are from Linkage Genetics, 1515 West 2200 South, Suite C, Salt Lake City, Utah 84119.

TABLE 10

RFLP PROFILE OF 01IZB2

| PROBE/ENZYME COMBINATION | 01IZB2 | 01IBH2 | 3IIH6 |
|---|---|---|---|
| M0264H | H | H | H |
| M0306H | A | A | A |
| M1234H | I | I | I |
| M1238H | E | E | E |
| M1406H | B | B | B |
| M1B725E | B | F | B |
| M2297H | B | B | B |
| M2298E | C | C | C |
| M2402H | E | C | C |
| M3212S | C | A | C |
| M3247E | B | B | — |
| M3257S | A | A | A |
| M3446S | F | C | F |
| M4386H | D | D | D |
| M4396E | H | H | H |
| M4444H | A | A | A |
| M4UMC19H | A | A | A |
| M4UMC31S | D | D | D |
| M5295E | C | A | — |
| M6223E | B | C | C |
| M6252H | A | A | A |
| M6280H | E | G | C |
| M6373E | E | E | E |
| M7263E | B | A | A |
| M7391H | C | A | A |
| M7455H | B | B | B |
| M8107S | D | D | A |
| M8114E | G | F | B |
| M8585H | A | B | — |
| M8B2369S | D | D | — |
| M8UMC48E | C | — | A |
| M9209E | A | A | A |
| M2UMC34H | F | D | — |
| M9B713S | A | A | A |
| M9UMC94H | B | E | — |
| M3UM121X | A | A | — |
| M0UMC13O | C | C | — |

*Probes used to detect RFLPs are from Linkage Genetics, 1515 West 2200 South, Suite C, Salt Lake City, Utah 84119.

Another aspect of this invention is a plant genetic complement characterized by a genetic isozyme typing profile. Isozymes are forms of proteins that are distinguishable, for example, on starch gel electrophoresis, usually by charge and/or molecular weight. The techniques and nomenclature for isozyme analysis are described in, Stuber et al. (1988), which is incorporated by reference.

A standard set of loci can be used as a reference set. Comparative analysis of these loci is used to compare the purity of hybrid seeds, to assess the increased variability in hybrids compared to inbreds, and to determine the identity of seeds, plants, and plant parts. In this respect, an isozyme reference set can be used to develop genotypic "fingerprints."

Tables 11 and 12 list the identifying numbers of the alleles at isozyme loci types. Tables 11 and 12 represent the exemplary genetic isozyme typing profiles for 01DIB2 and 01IZB2, respectively.

TABLE 11

ISOZYME PROFILE OF 01DIB2

| | ISOZYME ALLELE | | |
|---|---|---|---|
| LOCUS | 01DIB2 | 2FACC | 91BMA2 |
| Acph-1 | 2 | 2 | 2 |
| Adh-1 | 4 | 4 | 4 |
| Cat-3 | 9 | 9 | 9 |
| Got-1 | 4 | 4 | 4 |
| Got-2 | 4 | 4 | 4 |
| Got-3 | 4 | 4 | 4 |
| Idh-1 | 4 | 4 | 4 |
| Idh-2 | 6 | 6 | 6 |
| Mdh-1 | 6 | 6 | 6* |
| Mdh-2 | 3.5 | 3.5 | 6 |
| Mdh-3 | 16 | 16 | 16 |
| Mdh-4 | 12 | 12 | 12 |
| Mdh-5 | 12 | 12 | 12 |
| 6-Pgd-1 | 3.8 | 3.8 | 3.8 |
| 6-Pgd-2 | 5 | 5 | 5 |
| Pgm-1 | 9 | 9 | 9 |
| Pgm-2 | 4 | 4 | 4 |
| Phi-1 | 4 | 4 | 4 |
| # of seeds analyzed: | 6 | 12 | 6 |

*Allele is probably a 6, but null cannot be ruled out.

TABLE 12

ISOZYME PROFILE OF 01IZB2

| | ISOZYME ALLELE | | |
|---|---|---|---|
| LOCUS | 01DIB2 | 2FACC | 91BMA2 |
| Acph-1 | 2 | 2 | 2 |
| Adh-1 | 4 | 4 | 4 |
| Cat-3 | 9 | 9 | 9 |
| Got-1 | 4 | 4 | 4 |
| Got-2 | 4 | 4 | 4 |
| Got-3 | 4 | 4 | 4 |
| Idh-1 | 4 | 4 | 4 |
| Idh-2 | 6 | N/S* | 6 |
| Mdh-1 | 1 | 6 | 6 |
| Mdh-2 | 3.5 | N/S* | 3.5 |
| Mdh-3 | 16 | 16 | 16 |
| Mdh-4 | 12 | 12 | 12 |
| Mdh-5 | 12 | 12 | 12 |
| 6-Pgd-1 | 3.8 | 3.8 | 3.8 |
| 6-Pgd-2 | 5 | 5 | 5 |
| Pgm-1 | 9 | 9 | 9 |
| Pgm-2 | 4 | 4 | 4 |
| Phi-1 | 4 | 4 | 4 |
| # of seeds analyzed: | 12 | 12 | 6 |

*N/S = enzyme system was not scorable.

The present invention also contemplates a hybrid genetic complement formed by the combination of a haploid genetic complement of the corn plant 01DIB2 or 01IZB2, with a haploid genetic complement of a second corn plant. Means for combining a haploid genetic complement from any of the foregoing inbreds with another haploid genetic complement can be any method hereinbefore for producing a hybrid plant from 01DIB2 or 01IZB2. It is also contemplated that a hybrid genetic complement can be prepared using in vitro regeneration of a tissue culture of a hybrid plant of this invention.

A hybrid genetic complement contained in the seed of a hybrid derived from 01DIB2 or 01IZB2 is a further aspect of this invention. An exemplary hybrid genetic complement is the genetic complement of the hybrid 2003929.

Table 13 shows the identifying numbers of the alleles for the hybrid 2003929, which are exemplary RFLP genetic marker profiles for the hybrid derived from the inbreds of the present invention.

Table 13 concerns 2003929, which has both 01DIB2 and 01IZB2 as inbred parents.

TABLE 13

RFLP PROFILE OF 2003929

| PROBE/ENZYME COMBINATION | ALLELIC PAIR |
| --- | --- |
| M0264H | GH |
| M0306H | AA |
| M1234H | DI |
| M1238H | EA |
| M1406H | AB |
| MIB725E | BH |
| M2402H | EE |
| M3212S | AC |
| M3247E | BB |
| M3257S | AB |
| M3446S | BF |
| M4386H | BD |
| M4396E | HH |
| M4444H | AB |
| M4UMC19H | AA |
| M4UMC31S | AD |
| M6223E | AB |
| M6280H | EE |
| M6373E | AE |
| M7263E | BC |
| M7391H | CC |
| M7455H | AB |
| M8114E | BG |
| M8268H | BL |
| M8585H | AB |
| M8B2369S | BD |
| M9209E | AC |
| M9B713S | AA |
| M9UMC94H | BE |
| M3UM121X | AC |
| M0UMC130 | CH |

*Probes used to detect RFLPs are from Linkage Genetics, 1515 West 2200 South, Suite C, Salt Lake City, Utah 84119.

The exemplary hybrid genetic complements of hybrid 2003929, may also be assessed by genetic isozyme typing profiles using a standard set of loci as a reference set, using, e.g., the same, or a different, set of loci to those described above. Table 14 lists the identifying numbers of the alleles at isozyme loci types and present the exemplary genetic isozyme typing profiles for the hybrid 2003929, which is an exemplary hybrid derived from the inbreds of the present invention.

Table 14 concerns 2003929, which has both 01DIB2 and 01IZB2 as inbred parents.

TABLE 14

ISOZYME GENOTYPE FOR HYBRID 2003929

| LOCUS | ISOZYME ALLELE |
| --- | --- |
| Acph-1 | 2 |
| Adh-1 | 4 |
| Cat-3 | 9 |
| Got-1 | 4 |
| Got-2 | 4 |
| Got-3 | 4 |
| Idh-1 | 4 |
| Idh-2 | 6 |
| Mdh-1 | 1/6 |
| Mdh-2 | 3.5 |
| Mdh-3 | 16 |
| Mdh-4 | 12 |
| Mdh-5 | 12 |
| 6-Pgd-1 | 3.8 |
| 6-Pgd-2 | 5 |
| Pgm-1 | 9 |
| Pgm-2 | 4 |
| Phi-1 | 4 |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications and alterations may be applied to the composition, methods, and in the steps or in the sequence of steps of the methods described herein, without departing from the true concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Armstrong and Green, "Establishment and Maintenance of Friable Embryogenic Maize Callus and the Involvement of L-Proline," *Planta,* 164:207–214, 1985.

Conger et al., "Somatic Embryogenesis from Cultured Leaf Segments of Zea Mays," *Plant Cell Reports,* 6:345–347, 1987.

Duncan et al., "The Production of Callus Capable of Plant Regeneration from Immature Embryos of Numerous Zea Mays Genotypes," *Planta,* 165:322–332, 1985.

Fehr (ed.), *Principles of Cultivar Development, Vol. 1: Theory and Technique,* pp. 360–376, 1987.

Gaillard et al., "Optimization of Maize Microspore Isolation and Culture Condition for Reliable Plant Regeneration," *Plant Cell Reports,* 10(2):55, 1991.

Gordon-Kamm et al., "Transformation of Maize Cells and Regeneration of Fertile Transgenic Plants," *The Plant Cell,* 6:603–618, 1990.

Green and Rhodes, "Plant Regeneration in Tissue Cultures of Maize," Maize for Biological Research, Plant Molecular Biology Association, pp. 367–372, 1982.

Jensen, "Chromosome Doubling Techniques in Haploids," Haploids and Higher Plants—Advances and Potentials, Proceedings of the First International Symposium, University of Guelph, Jun. 10–14, 1974.

Nienhuis et al., "Restriction Fragment Length Polymorphism Analysis of Loci Associated with Insect Resistance in Tomato," *Crop Science,* 27:797–803, 1987.

Pace et al., "Anther Culture of Maize and the Visualization of Embryogenic Microspores by Fluorescent Microscopy," *Theoretical and Applied Genetics,* 73:863–869, 1987.

Poehlman and Sleper (eds.), *Breeding Field Crops,* 4th Ed., pp. 172–175, 1995.

Rao et al., "Somatic Embryogenesis in Glume Callus Cultures," *Maize Genetics Cooperation Newsletter,* Vol. 60, 1986.

Songstad et al. "Effect of 1-Aminocyclopropate-1-Carboxylic Acid, Silver Nitrate, and Norbornadiene on Plant Regeneration from Maize Callus Cultures," *Plant Cell Reports,* 7:262–265, 1988.

Stuber et al., "Techniques and scoring procedure for starch gel electrophoresis of enzymes of maize C. *Zea mays,* L.," *Tech. Bull.,* N. Carolina Agric. Res. Serv., Vol. 286, 1988.

Wan et al., "Efficient Production of Doubled Haploid Plants Through Colchicine Treatment of Anther-Derived Maize Callus," *Theoretical and Applied Genetics,* 77:889–892, 1989.

What is claimed is:

1. Inbred corn seed of the corn plant 01IZB2, a sample of said seed having been deposited under ATCC Accession No. 209836.

2. The inbred corn seed of claim 1, further defined as an essentially homogeneous population of inbred corn seed.

3. The inbred corn seed of claim 1, further defined as essentially free from hybrid seed.

4. An inbred corn plant produced by growing the seed of the inbred corn plant 01IZB2, a sample said seed having been deposited under ATCC Accession No. 209836.

5. Pollen of the plant of claim 4.

6. An ovule of the plant of claim 4.

7. An essentially homogeneous population of corn plants produced by growing the seed of the inbred corn plant 01IZB2, a sample of said seed having been deposited under ATCC Accession No. 209836.

8. A corn plant capable of expressing all the physiological and morphological characteristics of the inbred corn plant 01IZB2, a sample of the seed of said inbred corn plant 01IZB2 having been deposited under ATCC Accession No. 209836.

9. The corn plant of claim 8, further comprising a cytoplasmic factor conferring male sterility.

10. A tissue culture of regenerable cells of inbred corn plant 01IZB2, wherein the tissue regenerates plants capable of expressing all the physiological and morphological characteristics of corn plant 01IZB2, a sample of the seed of said inbred corn plant 01IZB2 having been deposited under ATCC Accession No. 209836.

11. The tissue culture of claim 10, wherein the regenerable cells comprise cells derived from embryos, protoplasts, meristematic cells, pollen, leaves, anthers, roots root tips, silk, flowers, kernels, ears, cobs, husks or stalks.

12. A corn plant regenerated from the tissue culture of claim 10, wherein said corn plant is capable of expressing all the physiological and morphological characteristics of corn plant 01IZB2, a sample of the seed of said inbred corn plant 01IZB2 having been deposited under ATCC Accession No. 209836.

13. An inbred corn plant cell of the corn plant of claim 8, said cell comprising:
   (a) an RFLP genetic marker profile in accordance with the profile shown in Table 10; or
   (b) a genetic isozyme typing profile in accordance with the profile shown in Table 12.

14. The inbred corn plant cell of claim 13, having an RFLP genetic marker profile in accordance with the profile shown in Table 10.

15. The inbred corn plant cell of claim 13, having a genetic isozyme typing profile in accordance with the profile shown in Table 12.

16. The inbred corn plant cell of claim 13, located within a corn plant or seed.

17. A process of preparing corn seed, comprising crossing a first parent corn plant with a second parent corn plant, wherein said first or second corn plant is the inbred corn plant 01IZB2, a sample of the seed of said inbred corn plant 01IZB2 having been deposited under ATCC Accession No. 209836, wherein seed is allowed to form.

18. The process of claim 17, further defined as a process of preparing hybrid corn seed, comprising crossing a first inbred corn plant with a second, distinct inbred corn plant, wherein said first or second inbred corn plant is the inbred corn plant 01IZB2, a sample of the seed of said inbred corn plant 01IZB2 having been deposited under ATCC Accession No. 209836.

19. The process of claim 18, wherein crossing comprises the steps of:
   (a) planting in pollinating proximity seeds of said first and second inbred corn plants;
   (b) cultivating the seeds of said first and second inbred corn plants into plants that bear flowers;
   (c) emasculating the male flowers of said first or second inbred corn plant to produce an emasculated corn plant;
   (d) allowing cross-pollination to occur between said first and second inbred corn plants; and
   (e) harvesting seeds produced on said emasculated corn plant.

20. The process of claim 19, further comprising growing said harvested seed to produce a hybrid corn plant.

21. Hybrid corn seed produced by the process of claim 18.

22. A hybrid corn plant produced by the process of claim 20.

23. The hybrid corn plant of claim 22, wherein the plant is a first generation ($F_1$) hybrid corn plant.

24. A seed of the $F_1$ hybrid corn plant of claim 23.

25. The corn plant of claim 8 further comprising a single gene conversion.

26. The single gene conversion of the corn plant of claim 25, where the gene is a dominant allele.

27. The single gene conversion of the corn plant of claim 25, where the gene is a recessive allele.

28. The single gene conversion corn plant of claim 25, where the gene confers herbicide resistance.

29. The single gene conversion of the corn plant of claim 25, where the gene confers insect resistance.

30. The single gene conversion of the corn plant of claim 25, where the gene confers resistance to bacterial, fungal, or viral disease.

31. The single gene conversion of the corn plant of claim 25, where the gene confers male sterility.

32. The single gene conversion of the corn plant of claim 25, where the gene confers waxy starch.

33. The corn plant of claim 25, wherein the single gene was stably inserted into a corn genome by transformation.

* * * * *